US00RE49349E

(19) United States
(12) Reissued Patent
Gregerson et al.

(10) Patent Number: US RE49,349 E
(45) Date of Reissued Patent: Dec. 27, 2022

(54) SYSTEMS AND METHODS FOR IMAGING LARGE FIELD-OF-VIEW OBJECTS

(71) Applicant: Medtronic Navigation, Inc., Louisville, CO (US)

(72) Inventors: Eugene A. Gregerson, Bolton, MA (US); Richard K. Grant, Sudbury, MA (US); Norbert Johnson, North Andover, MA (US)

(73) Assignee: Medtronic Navigation, Inc., Louisville, CO (US)

(21) Appl. No.: 16/531,388

(22) Filed: Aug. 5, 2019

Related U.S. Patent Documents

Reissue of:
(64) Patent No.: 9,724,058
Issued: Aug. 8, 2017
Appl. No.: 15/218,407
Filed: Jul. 25, 2016

U.S. Applications:
(60) Division of application No. 14/223,361, filed on Mar. 24, 2014, now Pat. No. 9,398,886, which is a
(Continued)

(51) Int. Cl.
*H05G 1/04* (2006.01)
*A61B 6/00* (2006.01)
(Continued)

(52) U.S. Cl.
CPC ..... *G01N 23/043* (2013.01); *A61B 6/032* (2013.01); *A61B 6/06* (2013.01); *A61B 6/4021* (2013.01);
(Continued)

(58) Field of Classification Search
CPC ... A61B 6/4405; A61B 6/4021; A61B 6/4085; A61B 6/4452; A61B 6/4233; A61B 6/032; A61B 6/06
See application file for complete search history.

(56) References Cited

U.S. PATENT DOCUMENTS 2,818,510 A 12/1957 Verse
3,432,657 A 3/1969 Salvin
(Continued)

FOREIGN PATENT DOCUMENTS

CN 1032188 C 7/1996
DE 8905588.8 U1 9/1990
(Continued)

OTHER PUBLICATIONS

2nd Chinese Office Action for Chinese Application No. 03806361.1; dated Apr. 23, 2010 (English Translation Only).
(Continued)

*Primary Examiner* — Patricia L Engle
(74) *Attorney, Agent, or Firm* — Harness, Dickey & Pierce, P.L.C.

(57) ABSTRACT

An imaging apparatus and related method comprising a detector located a distance from a source and positioned to receive a beam of radiation in a trajectory; a detector positioner that translates the detector to an alternate position in a direction that is substantially normal to the trajectory; and a beam positioner that alters the trajectory of the radiation beam to direct the beam onto the detector located at the alternate position.

18 Claims, 39 Drawing Sheets

Related U.S. Application Data continuation of application No. 12/684,430, filed on Jan. 8, 2010, now Pat. No. 8,678,647, which is a continuation of application No. 11/522,794, filed on Sep. 18, 2006, now Pat. No. 7,661,881, which is a continuation of application No. 10/392,365, filed on Mar. 18, 2003, now Pat. No. 7,108,421.

(60) Provisional application No. 60/366,062, filed on Mar. 19, 2002.

(51) Int. Cl.

| | |
|---|---|
| ***A61B 6/03*** | (2006.01) |
| ***G01N 23/04*** | (2018.01) |
| ***A61B 6/06*** | (2006.01) |
| ***G01N 23/046*** | (2018.01) |

(52) U.S. Cl.

CPC ..... *A61B 6/4085* (2013.01); *A61B 6/4233* (2013.01); *A61B 6/4405* (2013.01); *A61B 6/4452* (2013.01); *G01N 23/046* (2013.01); *G01N 2223/419* (2013.01)

(56) References Cited

U.S. PATENT DOCUMENTS

| | | | | |
|---|---|---|---|---|
| 3,549,885 | A | | 12/1970 | Andersson |
| 3,617,749 | A | | 11/1971 | Massiot |
| 3,924,129 | A | | 12/1975 | LeMay |
| 4,103,169 | A | | 7/1978 | Hounsfield |
| 4,200,799 | A | | 4/1980 | Saito |
| 4,210,815 | A | | 7/1980 | Riehl |
| 4,352,986 | A | | 10/1982 | Pfeiler |
| 4,355,409 | A | | 10/1982 | Amplatz |
| 4,442,489 | A | | 4/1984 | Wagner |
| 4,481,656 | A | | 11/1984 | Janssen et al. |
| 4,636,952 | A | | 1/1987 | Crawford |
| 4,741,015 | A | | 4/1988 | Charrier |
| 4,803,714 | A | | 2/1989 | Vlasbloem |
| 4,810,881 | A | | 3/1989 | Berger et al. |
| 4,817,121 | A | | 3/1989 | Shimizu et al. |
| 4,829,252 | A | | 5/1989 | Kaufman |
| 4,853,946 | A | | 8/1989 | Elliott et al. |
| 4,875,228 | A | | 10/1989 | Archer |
| 4,884,293 | A | | 11/1989 | Koyama |
| 4,935,949 | A | | 6/1990 | Fujita et al. |
| 4,955,046 | A | | 9/1990 | Siczek et al. |
| 4,982,415 | A | | 1/1991 | Shibata et al. |
| 4,987,585 | A | | 1/1991 | Kidd et al. |
| 5,014,292 | A | | 5/1991 | Siczek et al. |
| 5,014,293 | A | | 5/1991 | Boyd et al. |
| 5,023,899 | A | | 6/1991 | Ohlson |
| 5,032,990 | A | | 7/1991 | Eberhard et al. |
| D323,386 | S | | 1/1992 | Perusek |
| 5,084,908 | A | | 1/1992 | Alberici et al. |
| 5,095,501 | A | | 3/1992 | Kobayashi |
| 5,097,497 | A | | 3/1992 | Deucher et al. |
| 5,159,622 | A | | 10/1992 | Sakaniwa et al. |
| 5,164,973 | A | | 11/1992 | Takahashi et al. |
| 5,187,659 | A | | 2/1993 | Eberhard et al. |
| 5,265,610 | A | | 11/1993 | Darrow et al. |
| 5,287,274 | A | | 2/1994 | Saint Felix et al. |
| D345,606 | S | | 3/1994 | Perusek |
| 5,319,693 | A | | 6/1994 | Eberhard et al. |
| 5,390,112 | A | | 2/1995 | Tam |
| 5,448,607 | A | | 9/1995 | McKenna |
| 5,448,608 | A | | 9/1995 | Swain et al. |
| 5,452,337 | A | | 9/1995 | Endo et al. |
| 5,499,415 | A | | 3/1996 | McKenna |
| 5,515,416 | A | | 5/1996 | Siczek et al. |
| 5,583,909 | A | | 12/1996 | Hanover |
| 5,592,523 | A | | 1/1997 | Tuy et al. |
| 5,598,453 | A | | 1/1997 | Baba et al. |
| 5,617,465 | A | | 4/1997 | Bucher |
| 5,625,660 | A | | 4/1997 | Tuy |
| 5,638,419 | A | | 6/1997 | Ingwersen |
| 5,661,772 | A | | 8/1997 | Bar et al. |
| 5,668,846 | A | | 9/1997 | Fox et al. |
| 5,740,222 | A | | 4/1998 | Fujita et al. |
| 5,740,224 | A | | 4/1998 | Muller et al. |
| 5,745,545 | A | | 4/1998 | Hughes |
| 5,784,428 | A | | 7/1998 | Schmidt |
| 5,802,138 | A | | 9/1998 | Glasser et al. |
| 5,838,765 | A | * | 11/1998 | Gershman ..... A61B 6/0421 378/146 |
| 5,912,943 | A | | 6/1999 | Deucher et al. |
| RE36,415 | E | | 11/1999 | McKenna |
| 6,041,097 | A | | 3/2000 | Roos et al. |
| 6,113,264 | A | | 9/2000 | Watanabe |
| 6,130,930 | A | | 10/2000 | Tam |
| 6,147,352 | A | | 11/2000 | Ashburn |
| 6,169,780 | B1 | | 1/2001 | Yoshimura et al. |
| 6,181,769 | B1 | | 1/2001 | Hoheisel et al. |
| 6,203,196 | B1 | | 3/2001 | Meyer et al. |
| 6,212,251 | B1 | | 4/2001 | Tomura et al. |
| 6,215,841 | B1 | | 4/2001 | Hsieh |
| 6,285,733 | B1 | | 9/2001 | Proksa et al. |
| 6,289,073 | B1 | | 9/2001 | Sasaki et al. |
| 6,314,157 | B1 | | 11/2001 | Tachizaki |
| 6,322,251 | B1 | | 11/2001 | Ballhaus et al. |
| 6,324,246 | B1 | | 11/2001 | Ruimi |
| 6,325,537 | B1 | | 12/2001 | Watanabe |
| 6,374,937 | B1 | | 4/2002 | Galando et al. |
| 6,396,898 | B1 | | 5/2002 | Saito et al. |
| 6,435,715 | B1 | | 8/2002 | Betz et al. |
| 6,442,235 | B2 | | 8/2002 | Koppe et al. |
| 6,480,564 | B1 | | 11/2002 | Kim et al. |
| 6,484,049 | B1 | | 11/2002 | Seeley et al. |
| 6,487,267 | B1 | | 11/2002 | Wolter |
| 6,496,558 | B2 | | 12/2002 | Graumann |
| 6,519,312 | B1 | | 2/2003 | Tybinkowski et al. |
| 6,546,068 | B1 | | 4/2003 | Shimura |
| 6,580,777 | B1 | | 6/2003 | Ueki et al. |
| 6,582,120 | B2 | | 6/2003 | Schomberg |
| 6,590,953 | B2 | | 7/2003 | Suzuki et al. |
| 6,609,826 | B1 | | 8/2003 | Fujii et al. |
| 6,614,871 | B1 | | 9/2003 | Kobiki et al. |
| 6,619,840 | B2 | | 9/2003 | Rasche et al. |
| 6,742,929 | B2 | | 6/2004 | Horbaschek |
| 6,771,732 | B2 | | 8/2004 | Xiao et al. |
| 6,845,144 | B2 | | 1/2005 | Nishide et al. |
| 6,869,217 | B2 | | 3/2005 | Rasche et al. |
| 6,940,941 | B2 | | 9/2005 | Gregerson et al. |
| 6,990,170 | B2 | | 1/2006 | Sugihara et al. |
| 7,001,045 | B2 | | 2/2006 | Gregerson et al. |
| 7,106,825 | B2 | * | 9/2006 | Gregerson ..... G06T 11/005 378/19 |
| 7,108,421 | B2 | * | 9/2006 | Gregerson ..... A61B 6/032 378/146 |
| 7,188,998 | B2 | | 3/2007 | Gregerson et al. |
| 7,338,207 | B2 | | 3/2008 | Gregerson et al. |
| 7,490,982 | B2 | | 2/2009 | Gregerson et al. |
| 7,661,881 | B2 | | 2/2010 | Gregerson et al. |
| 7,903,779 | B2 | | 3/2011 | Gregerson et al. |
| 7,965,811 | B1 | | 6/2011 | Gregerson et al. |
| 8,308,361 | B2 | | 11/2012 | Gregerson et al. |
| 8,678,647 | B2 | | 3/2014 | Gregerson et al. |
| 9,398,886 | B2 | | 7/2016 | Gregerson et al. |
| 9,724,058 | B2 | | 8/2017 | Gregerson et al. |
| 2002/0039403 | A1 | | 4/2002 | Oota |
| 2002/0154728 | A1 | | 10/2002 | Morita et al. |
| 2003/0016791 | A1 | | 1/2003 | Ukita |
| 2004/0125917 | A1 | | 7/2004 | Ross et al. |
| 2004/0170254 | A1 | | 9/2004 | Gregerson et al. |
| 2004/0223583 | A1 | | 11/2004 | Tsujii |
| 2004/0228434 | A1 | | 11/2004 | Tsujii |
| 2004/0240603 | A1 | | 12/2004 | Cai et al. |
| 2006/0120511 | A1 | | 6/2006 | Gregerson et al. |
| 2007/0086566 | A1 | | 4/2007 | Gregerson et al. |
| 2007/0104308 | A1 | | 5/2007 | Gregerson et al. |
| 2008/0013691 | A1 | | 1/2008 | Gregerson et al. |

(56) References Cited

U.S. PATENT DOCUMENTS

| | | | |
|---|---|---|---|
| 2008/0212743 | A1 | 9/2008 | Gregerson et al. |
| 2014/0205074 | A1 | 7/2014 | Gregerson et al. |

FOREIGN PATENT DOCUMENTS

| | | | |
|---|---|---|---|
| DE | 19535583 | A1 | 3/1997 |
| DE | 19839825 | C1 | 10/1999 |
| DE | 19845756 | A1 | 4/2000 |
| DE | 19927953 | A1 | 1/2001 |
| DE | 19928738 | A1 | 1/2001 |
| EP | 0231969 | A1 | 8/1987 |
| EP | 0471455 | A2 | 2/1992 |
| EP | 0564292 | A2 | 10/1993 |
| EP | 0810005 | A2 | 12/1997 |
| EP | 1090585 | A1 | 4/2001 |
| EP | 1106141 | A2 | 6/2001 |
| FR | 2304321 | | 10/1976 |
| FR | 2304321 | A1 | 10/1976 |
| GB | 2088670 | A | 6/1982 |
| JP | S5812411 | U | 1/1983 |
| JP | H02228946 | A | 9/1990 |
| JP | H03176033 | | 7/1991 |
| JP | H05168619 | A | 7/1993 |
| JP | H06169905 | A | 6/1994 |
| JP | H07250829 | A | 10/1995 |
| JP | H09304303 | A | 11/1997 |
| JP | H119583 | A | 1/1999 |
| JP | 11253435 | A | 9/1999 |
| JP | 2000070255 | A | 3/2000 |
| JP | 2000197627 | A | 7/2000 |
| JP | 2000312674 | A | 11/2000 |
| JP | 2001008929 | A | 1/2001 |
| JP | 2001204718 | A | 7/2001 |
| JP | 2001204720 | A | 7/2001 |
| JP | WO-03081220 | A2 | 10/2003 |
| JP | 2005517486 | A | 6/2005 |
| JP | 2005529648 | A | 10/2005 |
| JP | H06169905 | A | 6/2006 |
| JP | H06303526 | A | 11/2006 |
| JP | 04059893 | B2 | 3/2008 |
| JP | H08112277 | A | 5/2008 |
| WO | WO-9428971 | A2 | 12/1994 |
| WO | WO-9606561 | A1 | 3/1996 |
| WO | WO-01/00092 | A1 | 1/2001 |
| WO | WO-03070101 | A1 | 8/2003 |
| WO | WO-03077763 | A2 | 9/2003 |
| WO | 03081220 | A2 | 10/2003 |
| WO | WO-03103496 | A1 | 12/2003 |
| WO | WO-2004017832 | A2 | 3/2004 |
| WO | WO-2004019279 | A2 | 3/2004 |

OTHER PUBLICATIONS

2nd Japanese Office Action for Japanese Appl. No. JP 2003-575822, dated Feb. 23, 2010 (with English translation).

Appeal Decision for Japanese Application No. 2003-578905 dated May 18, 2010 (English translation).

Appeal Decision for Japanese Application No. 2003-578905; dated May 18, 2010 (No English Translation Available).

Argument and Amendment for Japanese Appl. No. JP 2003-575822, dated Aug. 5, 2009 (with English claims as amended).

Argument and Amendment for Japanese Appl. No. JP 2004-531152, dated Oct. 2, 2009 (with English claims as amended).

Argument and Amendment for Japanese Application No. 2004-510623; dated Apr. 13, 2010 (With English Translation of Amended Claims).

Communication pursuant to Article 94(3) EPC dated Aug. 6, 2014 for Application No. 10179317.2-1554.

Communication pursuant to Article 94(3) EPC for EP Application No. 141986828 dated Nov. 22, 2016 corresponding to PCT/US2003/008383.

Communication Pursuant to Article 94(3) EPC for European Appl. No. 07 020 404.5, dated Oct. 6, 2009.

Communication to Rule 69 EPC dated Jan. 18, 2016 for European Application No. 14198682.8-1554/2915488.

English language translation of JP11253435A (Siemens, assignee) 1991.

European Communication Pursuant to Article 94(3) EPC dated Aug. 6, 2014 for European application No. 10179317.2.

European Search Report for European Application No. EP 0702404.5, dated Jun. 30, 2008.

European Search Report for European Application No. EP 10157926.6, dated May 21, 2010.

Hasegawa "Dual-Modality Imaging of Function and Physiology" Acad Radiol 2002; 9:1305-1321.

Hein et al., "Double-Centering Method for Increasing Efficiency of Cone-Beam X-Ray CT Reconstruction," IEEE, pp. 1728, 2002.

International Preliminary Examination Report for Int'l Application No. PCT/US02/40132, dated Feb. 4, 2004.

International Preliminary Examination Report for Int'l Application No. PCT/US03/08143, dated Apr. 13, 2004.

International Preliminary Examination Report for Int'l Application No. PCT/US03/08383, dated Jun. 23, 2004.

International Preliminary Examination Report for Int'l Application No. PCT/US03/18398, dated Oct. 21, 2005.

International Preliminary Examination Report for Int'l Application No. PCT/US03/26021, dated Jul. 19, 2004.

International Preliminary Examination Report for Int'l Application No. PCT/US03/26120, dated Dec. 9, 2004.

International Search Report for Int'l Application No. FCT/US03/08383, dated Nov. 25, 2003.

International Search Report for Int'l Application No. PCT/US02/40132, dated Mar. 20, 2003.

International Search Report for Int'l Application No. PCT/US03/08143, dated Dec. 18, 2003.

International Search Report for Int'l Application No. PCT/US03/08143, dated Oct. 13, 2003.

International Search Report for Int'l Application No. PCT/US03/18398, dated Sep. 16, 2003.

International Search Report for Int'l Application No. PCT/US03/26021, dated Feb. 18, 2004.

International Search Report for Int'l Application No. PCT/US03/26120, dated May 21, 2004.

Iwata, K. et al., "Description of a Prototype Combined CT-SPECT System with a Single CdZnTE Detector", Nuclear Science Symposium Conference Record, 2000 IEEE , XP010556613, pp. 16-1-16-5.

Japanese Office Action for Application No. 2004-510623 dated Jun. 15, 2010 (English translation).

Japanese Office Action for Japanese Appl. No. JP 2003-575822, dated Feb. 17, 2009 (with English translation).

Japanese Office Action for Japanese Appl. No. JP 2004-510623, dated Oct. 20, 2009 (with English translation).

Japanese Office Action for Japanese Appl. No. JP 2004-531152, dated Apr. 7, 2009 (with English translation).

Kalki, K. et al, "A Combined SPECT and X-ray CT Medical Imaging System," SPIE, 2432: 367-375 (Jul. 1995).

Lang, T.F. et al., "A Prototype Emission-Transmission Imaging System", Proceedings of the Nuclear Science Symposium and Medical Imaging Conference, 1991 IEEE, XP010058199, pp. 1902-1906.

Lang, Thomas, F. et al., "Description of a Prototype Emission—Transmission Computed Tomography Imaging System", Journal of Nuclear Medicine, Society of Nuclear Medicine, 1992, XP002901050, pp. 1881-1887.

Ning, R et al., An Image Intensifier-Based Volume Tomographic Angiography Imaging System SPIE vol. 3032, pp. 238-247.

Van Metter "Physics of Medical Imaging" vol. 3032, Proceedings of SPIE, Feb. 23-25, 1997.

Written Opinion for Int'l Application No. PCT/US02/40132, dated Oct. 9, 2003.

Written Opinion for Int'l Application No. PCT/US03/08143, dated Nov. 24, 2003.

(56) References Cited

OTHER PUBLICATIONS

Written Opinion for Int'l Application No. PCT/US03/08383, dated Jan. 7, 2004.
Written Opinion for Int'l Application No. PCT/US03/18398, dated Jun. 24, 2005.
Written Opinion for Int'l Application No. PCT/US03/26120, dated Jul. 29, 2004.
Mng-Hsiu Su, et al.., "3D x-ray angiography: Study of factors affecting projection data consistency", Physics of Medical Imaging, Proceedings of SPIE, pp. 226-237, Feb. 23-25, 1997, vol. 3032.
U.S. Appl. No. 10/392,365, filed Mar. 18, 2003, Gregerson et al., U.S. Pat. No. 7,108,421.
U.S. Appl. No. 11/522,794, filed Sep. 18, 2006, Gregerson et al., U.S. Pat. No. 7,661,881.
U.S. Appl. No. 12/684,430, filed Jan. 8, 2010, Gregerson et al., U.S. Pat. No. 8,678,647.
U.S. Appl. No. 90/011,750, filed Jun. 17, 2011, Gregerson et al., U.S. Pat. No. 7,661,881 C1.
U.S. Appl. No. 14/223,361, filed Mar. 24, 2014, Gregerson et al., U.S. Pat. No. 9,398,886.
U.S. Appl. No. 15/218,407, filed Jul. 25, 2016, Gregerson et al., U.S. Pat. No. 9,724,058.
U.S. Appl. No. 16/532,892, filed Aug. 6, 2019, Gregerson et al.
U.S. Appl. No. 29/701,004, filed Aug. 7, 2019, Gregerson et al.
1st Chinese Office Action for Chinese Application No. 03806361.1; dated Mar. 28, 2008 (English Translation Only).

* cited by examiner

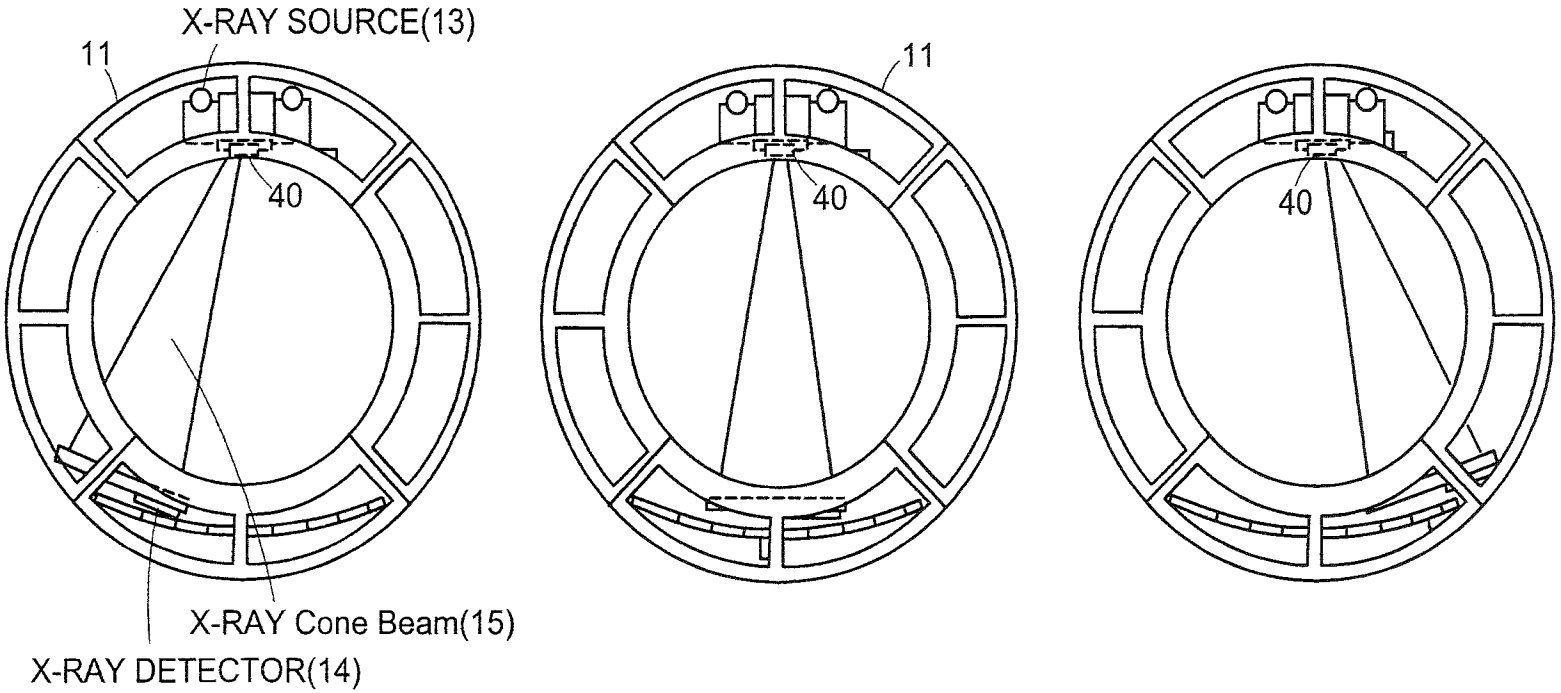
POSITION 1 FIG. 1A
POSITION 2 FIG. 1B
POSITION 3 FIG. 1C

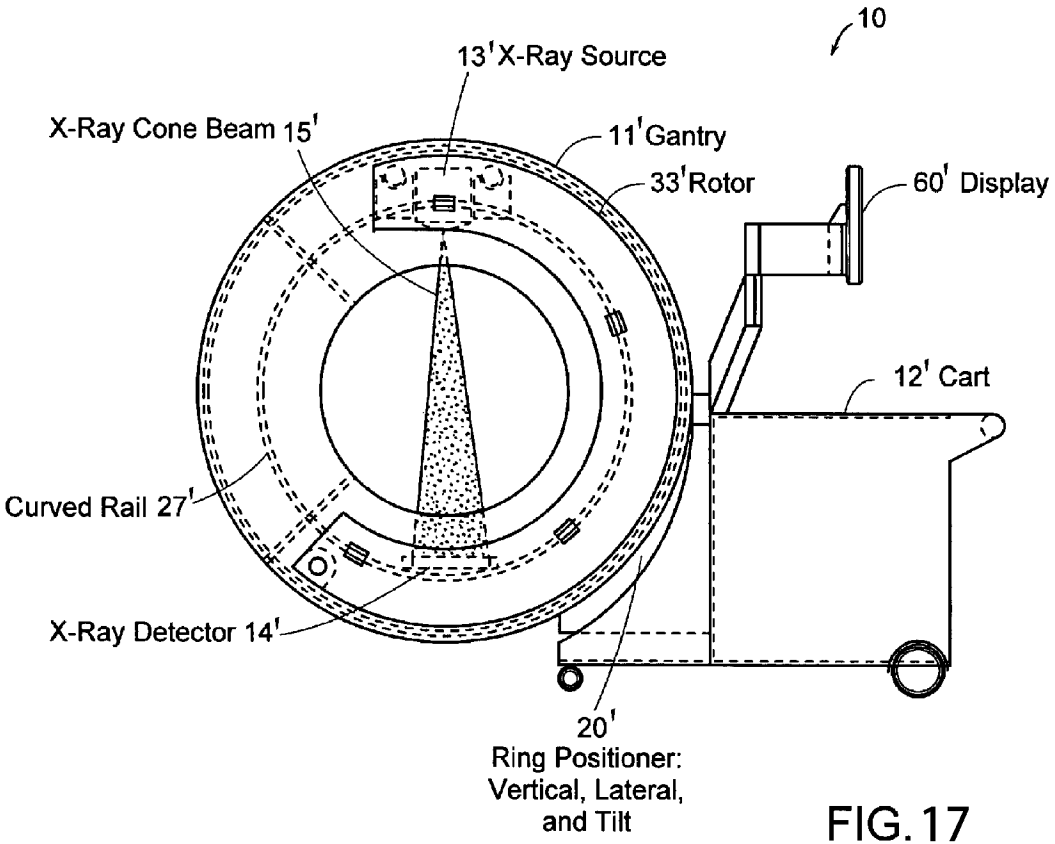
FIG. 17
NEW

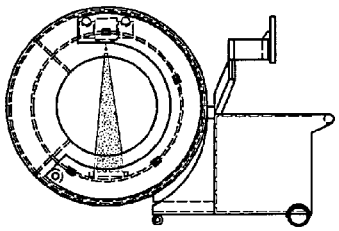
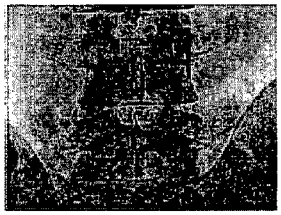
AP Position
FIG. 18A
NEW
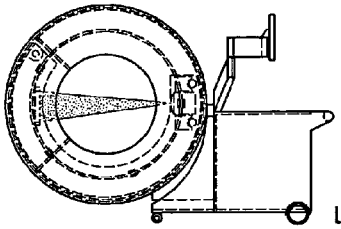
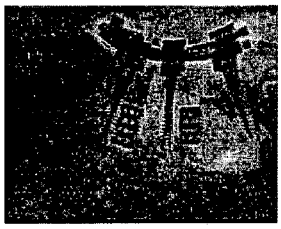
Lateral Position
FIG. 18B
NEW
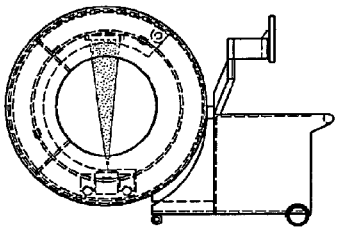
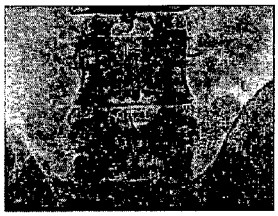
AP Position
FIG. 18C
NEW
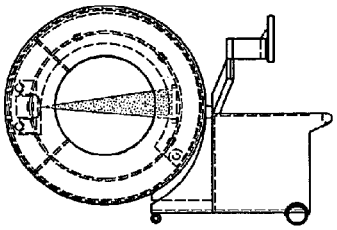
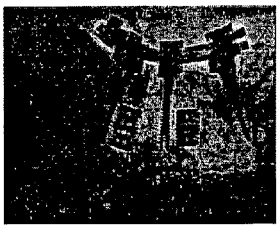
Lateral Position
FIG. 18D
NEW

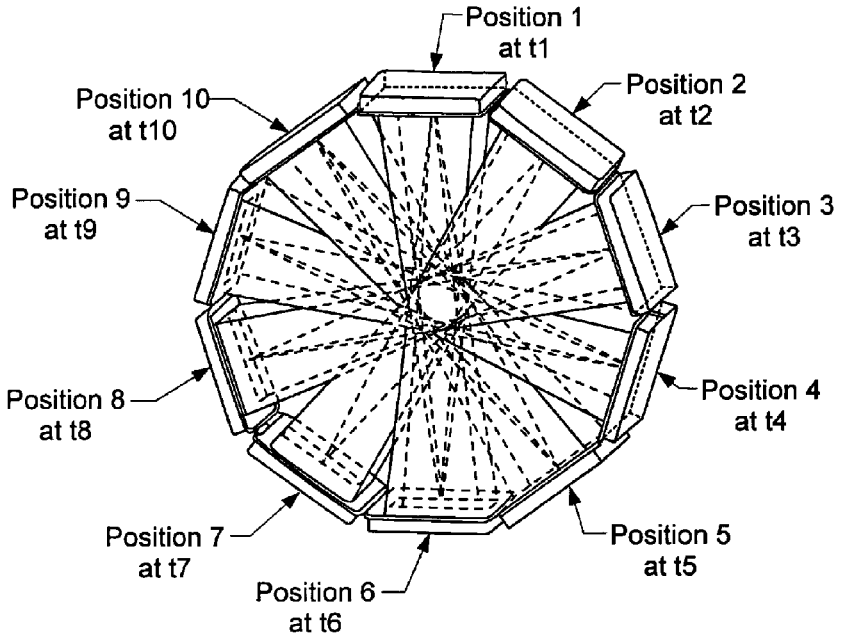
FIG. 19
NEW

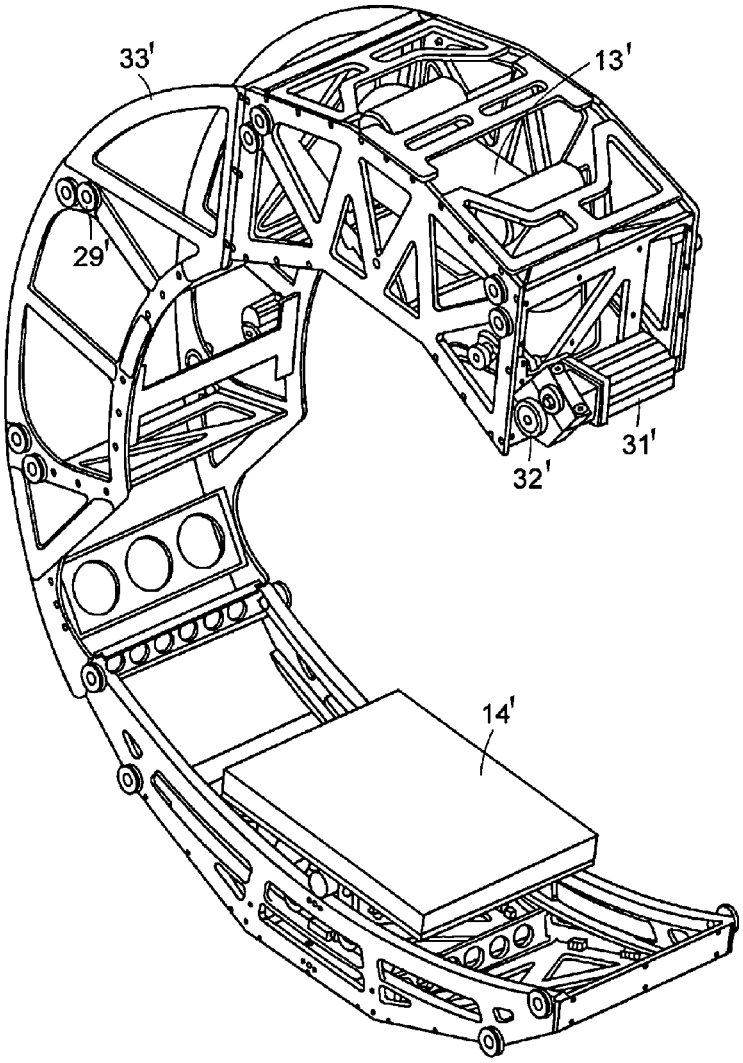
FIG. 20
NEW

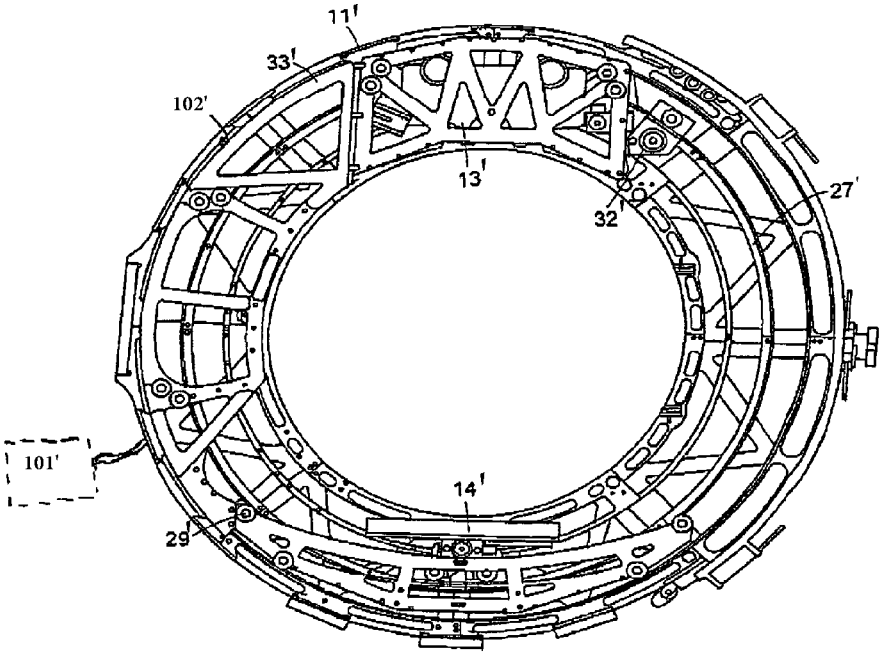
FIG. 21A
NEW

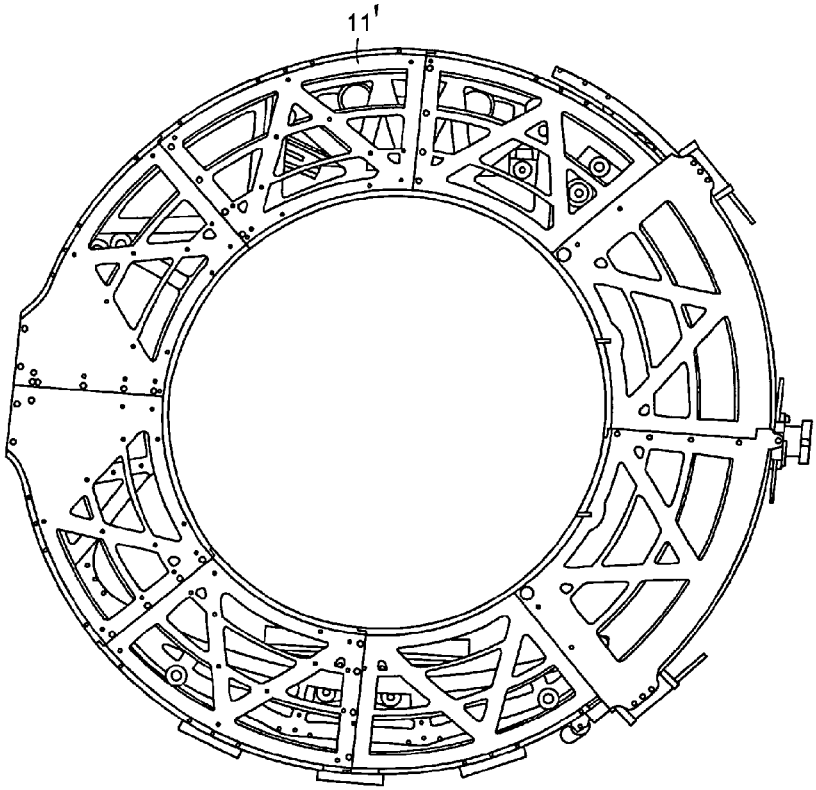
FIG. 21B
NEW

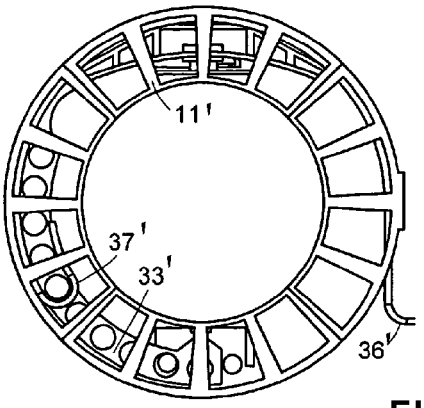
Rotor Angle (0°)
FIG. 22A
NEW
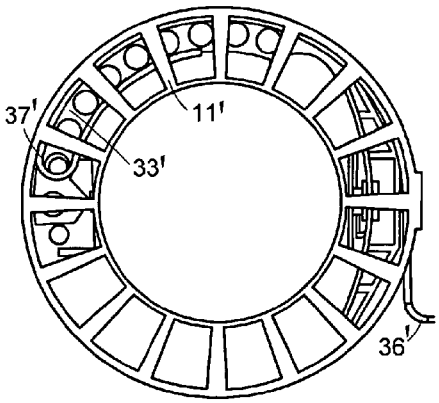
Rotor Angle (90°)
FIG. 22B
NEW
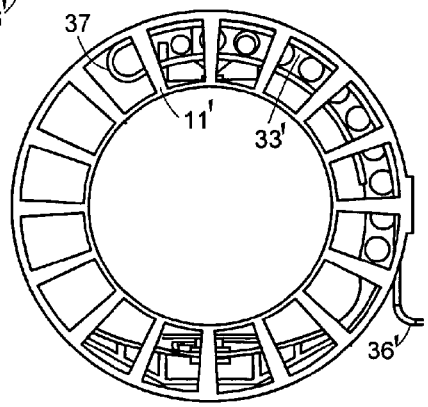
Rotor Angle (180°)
FIG. 22C
NEW

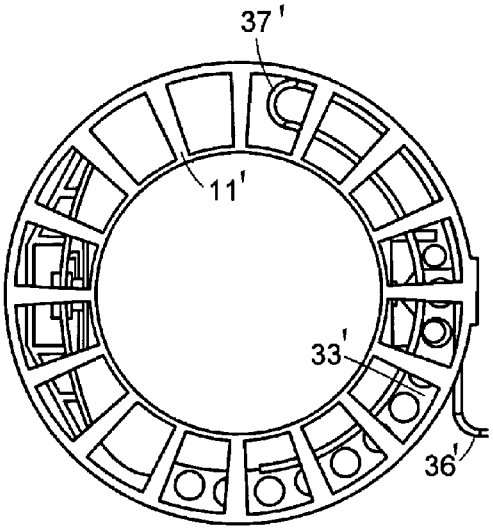
Rotor Angle (270°)
FIG. 22D
NEW
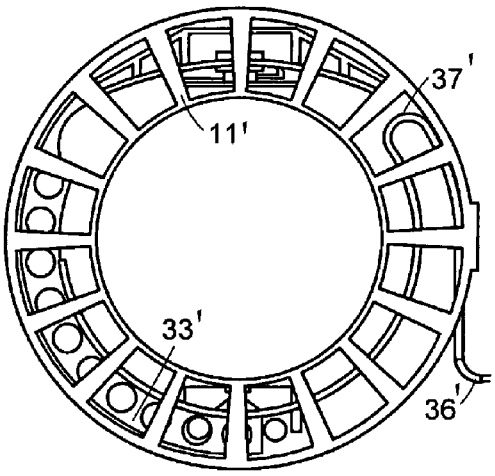
Rotor Angle (360°)
FIG. 22E
NEW

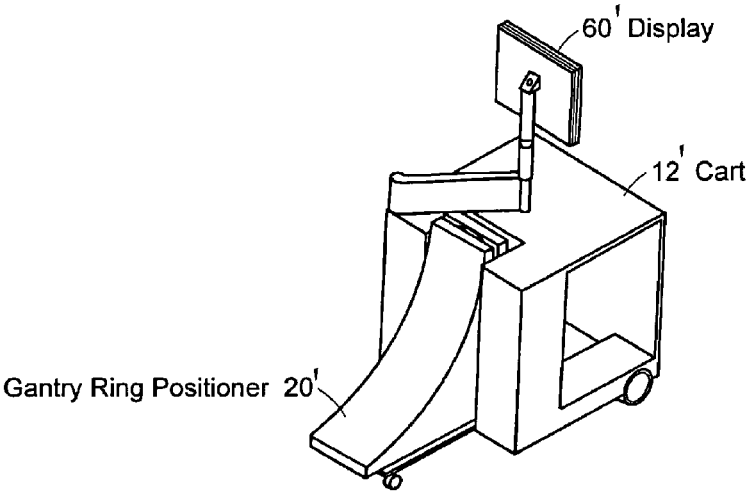
FIG. 23
NEW
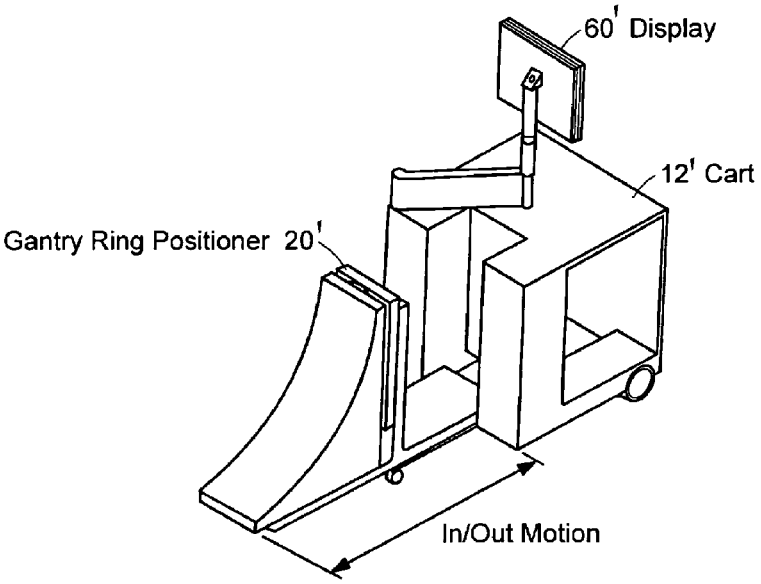
FIG. 24
NEW

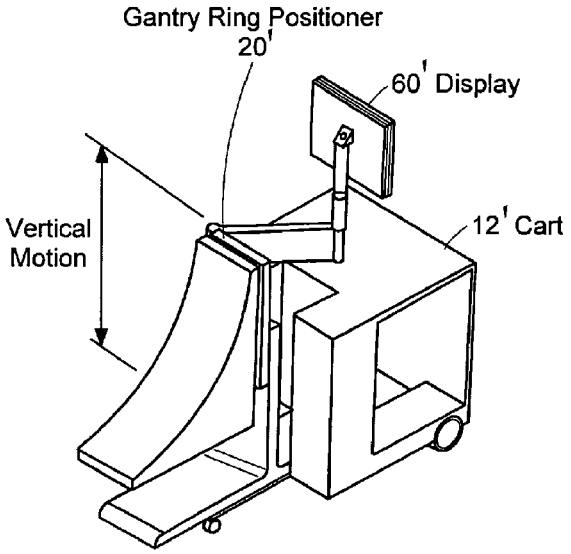
FIG. 25
NEW
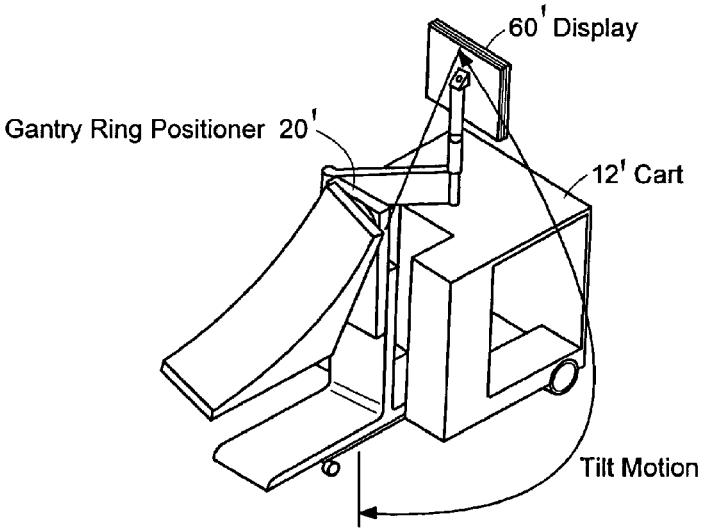
FIG. 26
NEW

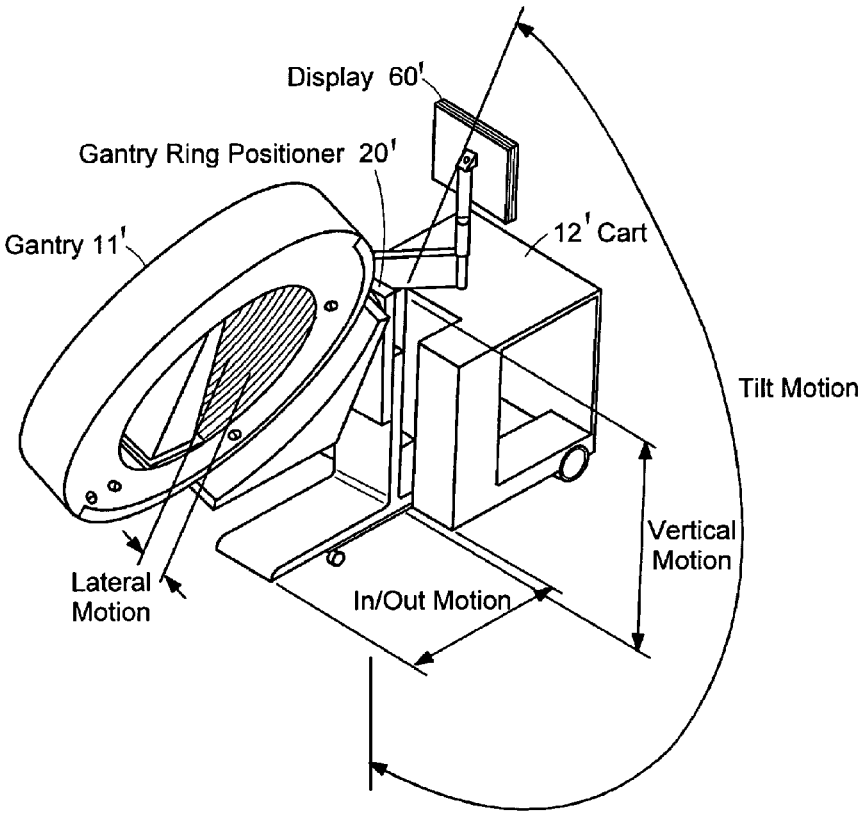
FIG. 27
NEW

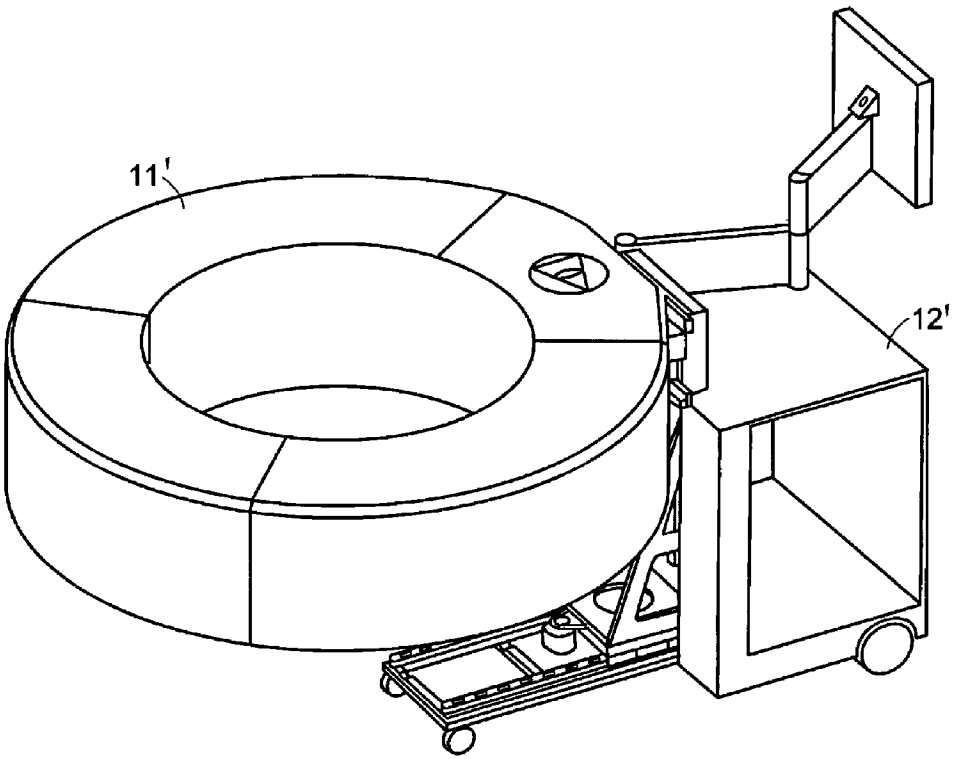
FIG. 28
NEW

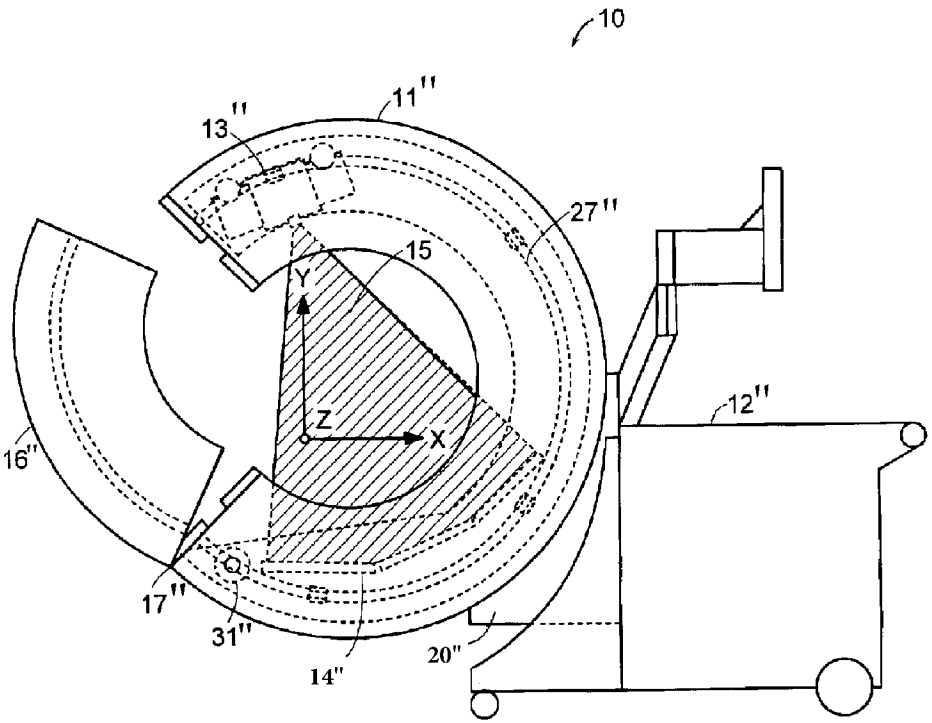
FIG. 29
NEW

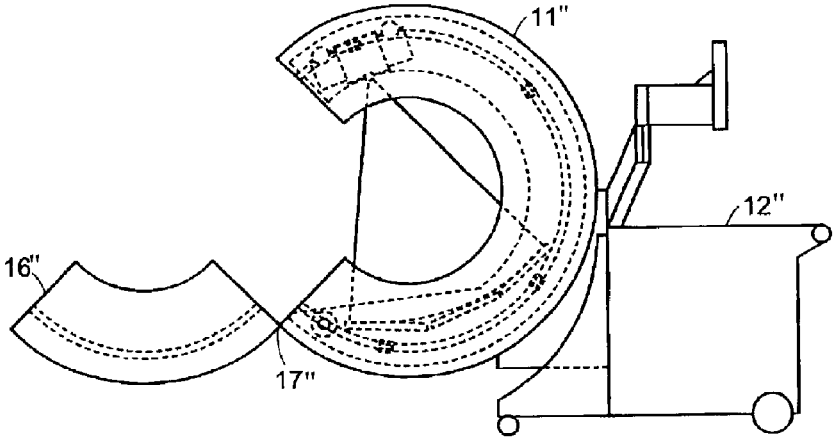
FIG. 30A
NEW
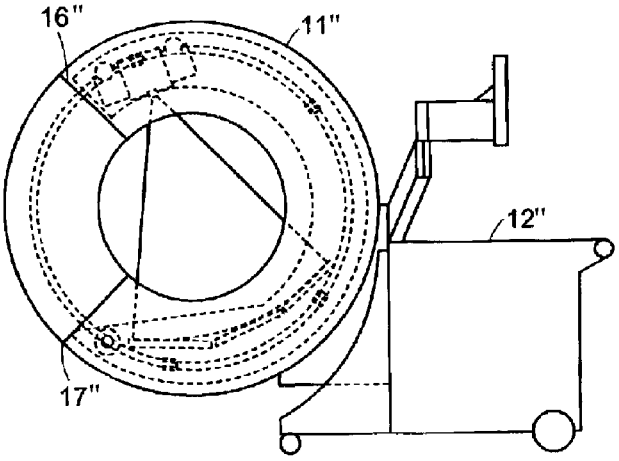
FIG. 30B
NEW

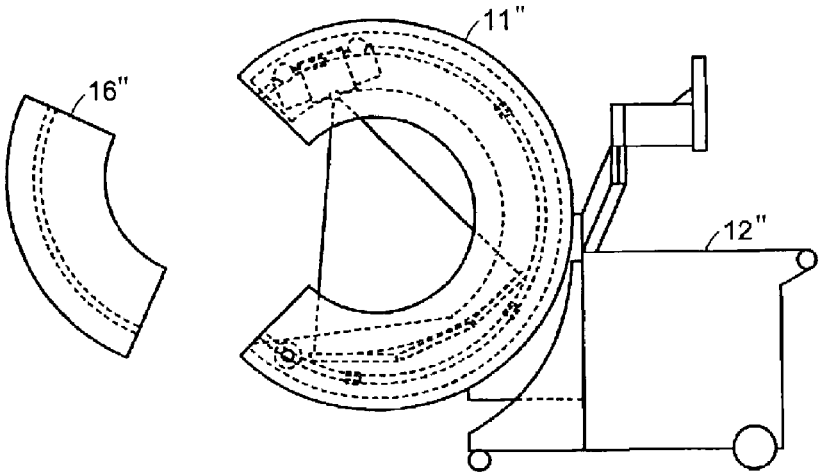
FIG. 31
NEW
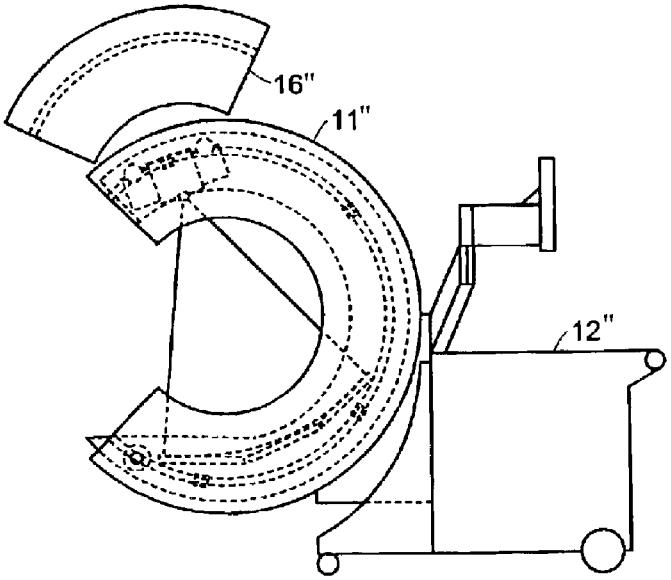
FIG. 32
NEW

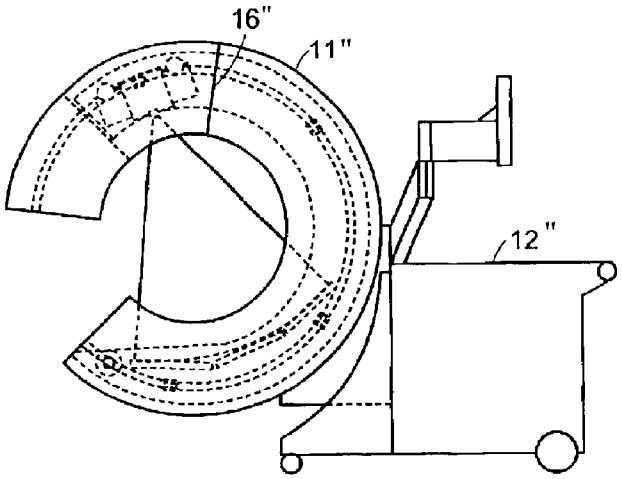
FIG. 33
NEW
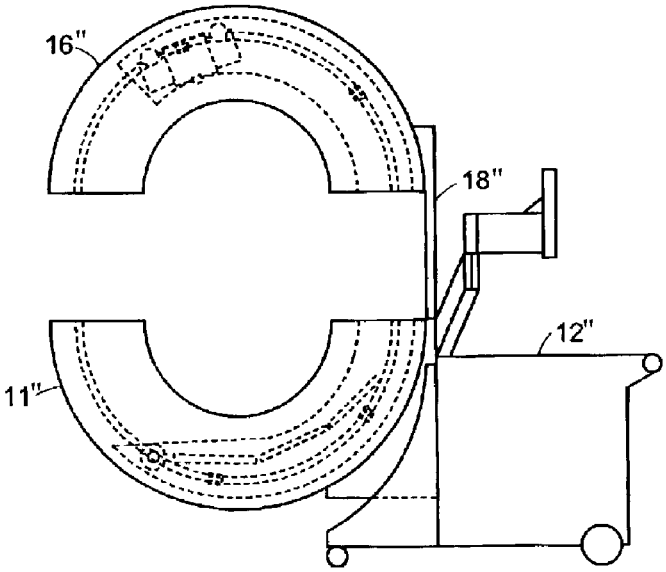
FIG. 34
NEW

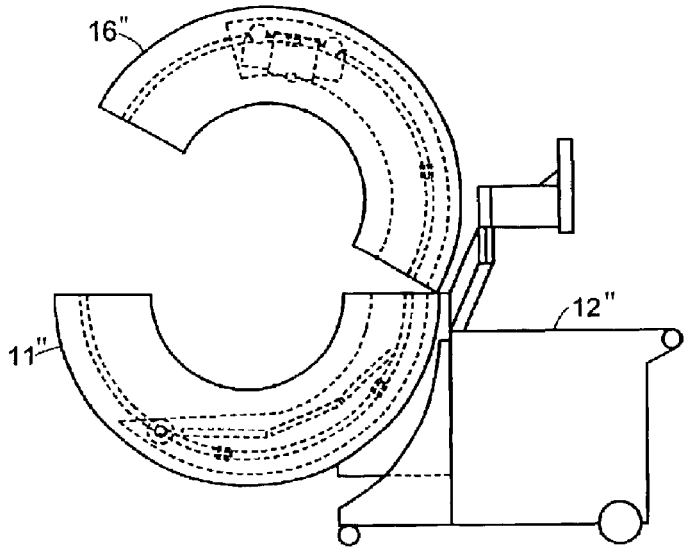
FIG. 35
NEW
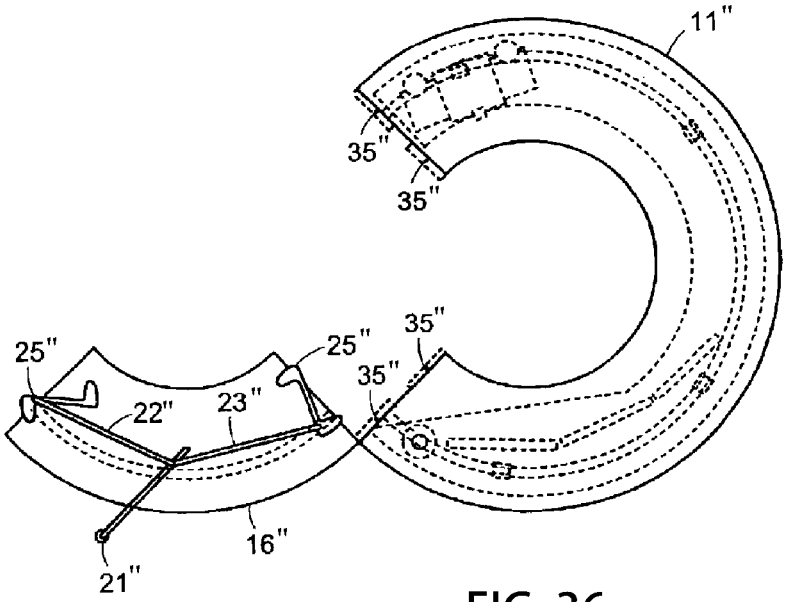
FIG. 36
NEW

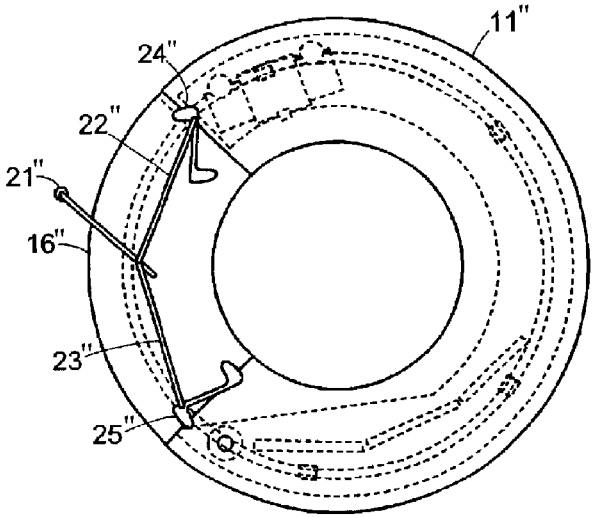
FIG. 37
NEW
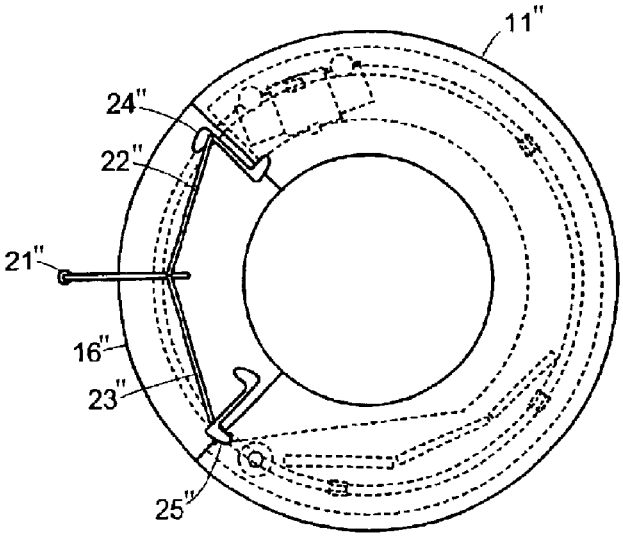
FIG. 38
NEW

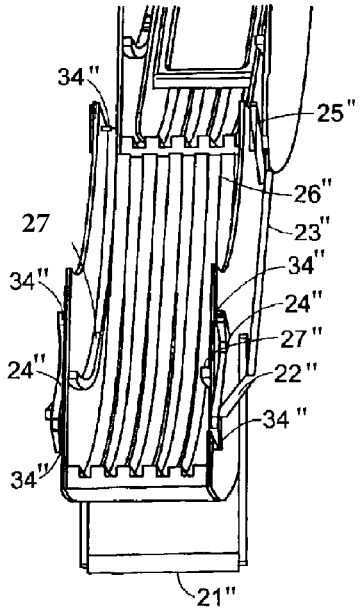
FIG. 39
NEW
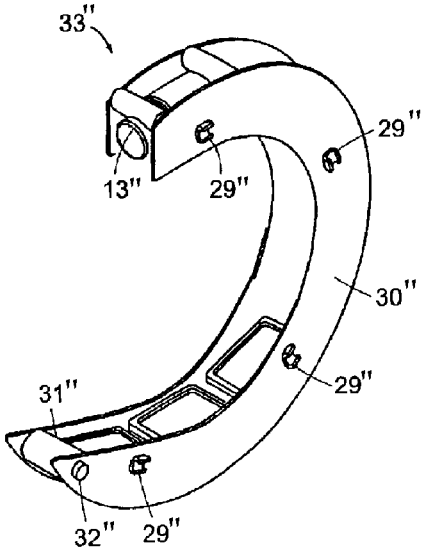
FIG. 40
NEW

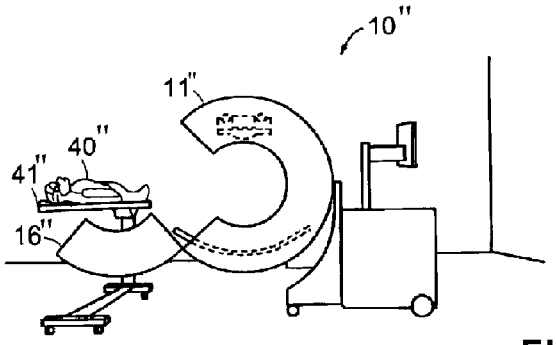
FIG. 41A
NEW
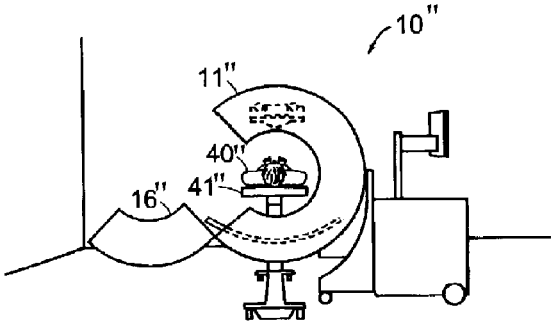
FIG. 41B
NEW
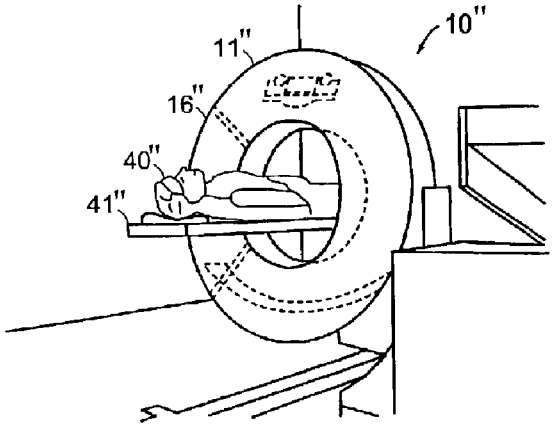
FIG. 41C
NEW

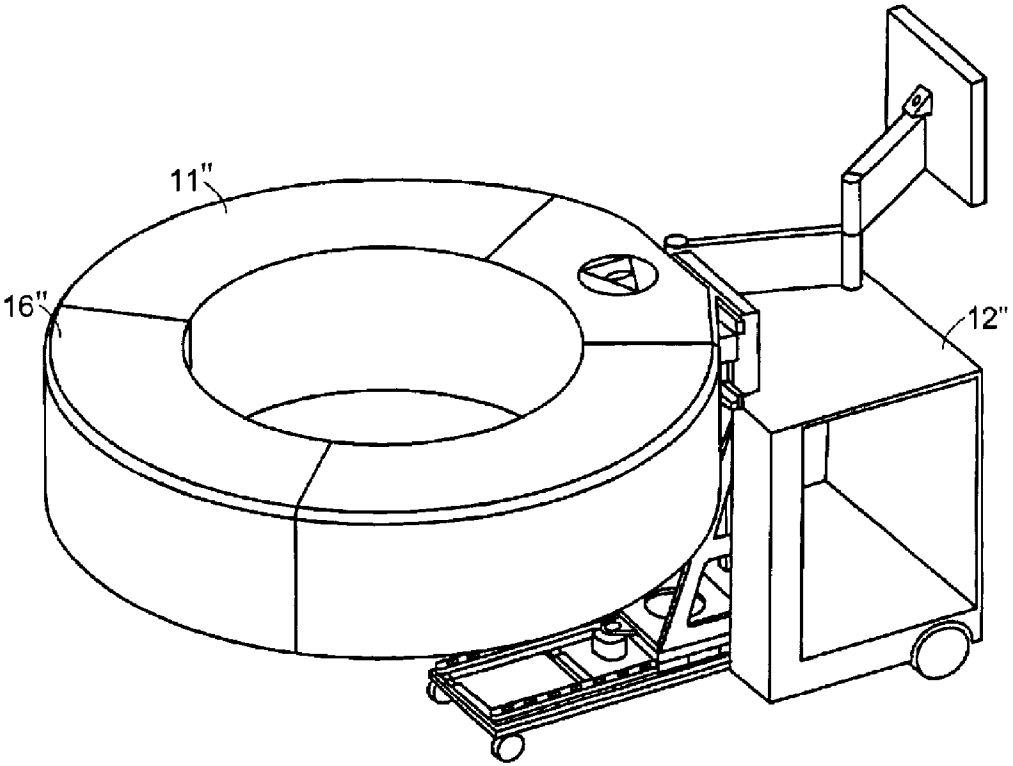
FIG. 42
NEW

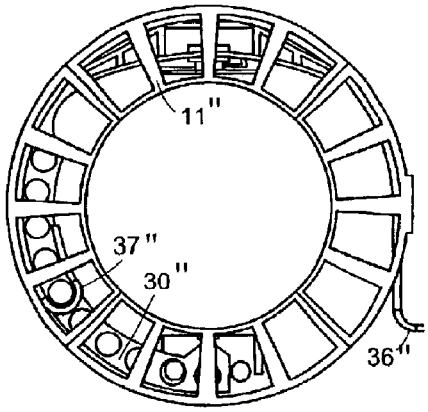
Rotor Angle(0°)
FIG. 43A
NEW
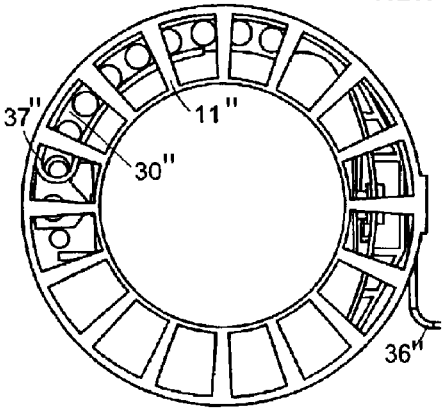
Rotor Angle(90°)
FIG. 43B
NEW
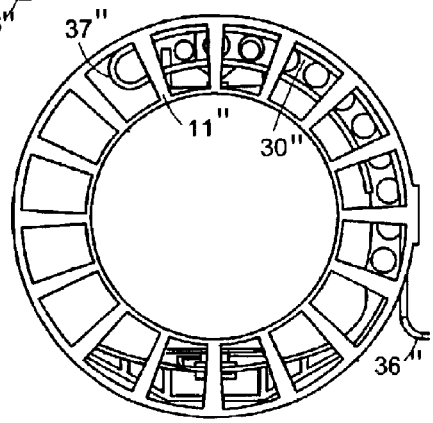
Rotor Angle(180°)
FIG. 43C
NEW

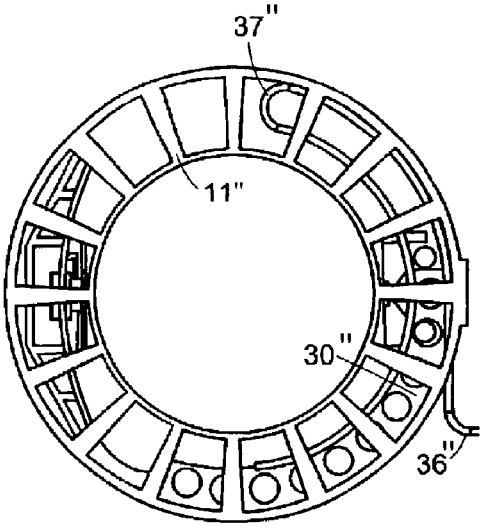
Rotor Angle(270°)
FIG. 43D
NEW
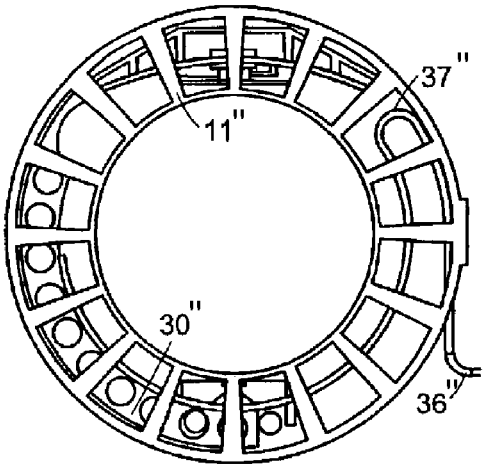
Rotor Angle(360°)
FIG. 43E
NEW

SYSTEMS AND METHODS FOR IMAGING LARGE FIELD-OF-VIEW OBJECTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This application is a reissue of U.S. Pat. No. 9,724,058 issued on Aug. 8, 2017. The disclosures of the above application is incorporated herein by reference.*

CROSS-REFERENCE TO RELATED APPLICATIONS

This application is a divisional of U.S. patent application Ser. No. 14/223,361 filed on Mar. 24, 2014, which is a continuation of U.S. patent application Ser. No. 12/684,430 filed on Jan. 8, 2010, now U.S. Pat. No. 8,678,647 issued on Feb. 16, 2010, which is a continuation of U.S. patent application Ser. No. 11/522,794 filed on Sep. 18, 2006, now U.S. Pat. No. 7,661,882 issued on Feb. 16, 2010, which is a continuation of U.S. patent application Ser. No. 10/392,365 filed on Mar. 18, 2003, now U.S. Pat. No. 7,108,421 issued on Sep. 19, 2006, which claims benefit of U.S. Patent Application No. 60/366,062 filed on Mar. 19, 2002. The entire disclosures of each of the above applications are incorporated herein by reference.

*Notice: More than one reissue application has been filed for the reissue of U.S. Pat. No. 9,724,058. The reissue applications are U.S. patent application Ser. No. 16/531,388 (the present application); U.S. patent application Ser. No. 16/532,892 which is a continuation reissue of U.S. patent application Ser. No. 16/531,388, now abandoned; and U.S. patent application Ser. No. 29/701,004, which is a continuation U.S. patent application Ser. No. 16/532,892.*

FIELD

The present disclosure relates to a system for imaging a subject, and particularly to a system for detecting image radiation.

BACKGROUND

This section provides background information related to the present disclosure which is not necessarily prior art.

In conventional computerized tomography for both medical and industrial applications, an x-ray fan beam and a linear array detector are employed to achieve two-dimensional axial imaging. The quality of these two-dimensional (2D) images is high, although only a single slice of an object can be imaged at a time. To acquire a three-dimensional (3D) data set, a series of 2D images are sequentially obtained in what is known as the "stack of slices" technique. One drawback to this method is that acquiring the 3D data set one slice at a time is an inherently slow process. There are other problems with this conventional tomographic technique, such as motion artifacts arising from the fact that the slices cannot be imaged simultaneously, and excessive exposure to x-ray radiation due to overlap of the x-ray projection areas.

Another technique for 3D computerized tomography is cone-beam x-ray imaging. In a system employing cone-beam geometry, an x-ray source projects a cone-shaped beam of x-ray radiation through the target object and onto a 2D area detector area. The target object is scanned, preferably over a 360-degree range, either by moving the x-ray source and detector in a scanning circle around the stationary object, or by rotating the object while the source and detector remain stationary. In either case, it is the relative movement between the source and object which accomplishes the scanning. Compared to the 2D "stack of slices" approach for 3D imaging, the cone-beam geometry is able to achieve 3D images in a much shorter time, while minimizing exposure to radiation. One example of a cone beam x-ray system for acquiring 3D volumetric image data using a flat panel image receptor is discussed in U.S. Pat. No. 6,041,097 to Roos, et al.

A significant limitation of existing cone-beam reconstruction techniques occurs, however, when the object being imaged is larger than the field-of-view of the detector, which is a quite common situation in both industrial and medical imaging applications. In this situation, some measured projections contain information from both the field of view of interest and from other regions of the object outside the field of view. The resulting image of the field of view of interest is therefore corrupted by data resulting from overlying material.

Several approaches have been proposed for imaging objects larger than the field-of-view of the imaging system. U.S. Pat. No. 5,032,990 to Eberhard et al., for example, discusses a technique for 2D imaging of an object which is so wide that a linear array detector is not wide enough to span the object or part which is to be viewed. The method involves successively scanning the object and acquiring partial data sets at a plurality of relative positions of the object, x-ray source, and detector array. U.S. Pat. No. 5,187,659 to Eberhard et al. discusses a technique for avoiding corrupted data when performing 3D CT on an object larger than the field of view. This technique involves scanning the object with multiple scanning trajectories, using one or more x-ray sources and detectors which rotate in different trajectories relative to the target object. Yet another technique is discussed in U.S. Pat. No. 5,319,693 to Ebarhard et al. This patent discusses simulating a relatively large area detector using a relatively small area detector by either moving the actual area detector relative to the source, or moving the object relative to the area detector. All of these techniques are characterized by complex relative movements between one or more x-ray sources, detectors, and the object being imaged. Furthermore, in each of these techniques, the target object is exposed to excessive x-ray radiation from regions of overlapping projections.

To date, there does not exist a radiation system for imaging large field-of-view objects in a simple and straightforward manner while minimizing the target object's exposure to radiation.

SUMMARY

This section provides a general summary of the disclosure, and is not a comprehensive disclosure of its full scope or all of its features.

The present invention relates to radiation-based imaging, including 3D computerized tomography (CT) and 2D planar x-ray imaging. In particular this invention relates to methods and systems for minimizing the amount of missing data and, at the same time, avoiding corrupted and resulting artifacts in image reconstruction when a cone-beam configuration is used to image a portion of an object that is larger than the field of view.

An imaging apparatus according to one aspect comprises a source that projects a beam of radiation in a first trajectory; a detector located a distance from the source and positioned to receive the beam of radiation in the first trajectory; an imaging area between the source and the detector, the radiation beam from the source passing through a portion of the imaging area before it is received at the detector; a detector positioner that translates the detector to a second position in a first direction that is substantially normal to the first trajectory; and a beam positioner that alters the trajectory of the radiation beam to direct the beam onto the detector located at the second position. The radiation source can be an x-ray cone-beam source, and the detector can be a two-dimensional flat-panel detector array.

By translating a detector of limited size along a line or arc opposite the radiation source, and obtaining object images at multiple positions along the translation path, an effectively large field-of-view may be achieved. In one embodiment, a detector positioner for translating the detector comprises a positioner frame that supports the detector and defines a translation path, and a motor that drives the detector as it translates within the positioner frame. A positioning feedback system, which can include a linear encoder tape and a read head, can be used to precisely locate and position the detector within the positioner frame. Other position encoder systems could also be used as the positioning feedback system, such as a rotary encoder and a friction wheel.

A radiation source, such as an x-ray source, includes a beam positioning mechanism for changing the trajectory of the emitted radiation beam from a fixed focal spot. This enables the beam to scan across an imaging region, and follow the path of a moving target, such as a translating detector array. In one aspect, the beam positioning mechanism of the present invention enables safer and more efficient dose utilization, as the beam positioner permits the beam to sequentially scan through limited regions of the target object, so that only the region within the field-of-view of the translating detector at any given time need be exposed to harmful radiation.

In one embodiment, a tilting beam positioning mechanism includes a frame which houses the radiation source, and a motorized system connected to both the frame and the source, where the motorized system pivots or tilts the source relative to the frame to alter the trajectory of the radiation beam projected from the source. In a preferred embodiment, the source is pivoted about the focal spot of the projected radiation beam. The motorized tilting system could include, for example, a linear actuator connected at one end to the fixed frame and at the other end to the source, where the length of the actuator controls the angle of tilt of the source, or a motorized pulley system for tilting the source. In another embodiment, a movable collimator is driven by a motor for changing the trajectory of the output beam.

In still another aspect, the invention includes means for rotating the source and translatable detector relative to an object to obtain images at different projection angles over a partial of full 360-degree scan. In one embodiment, the source and detector are housed in a gantry, such as a substantially O-shaped gantry ring, and are rotatable around the inside of the gantry ring. The source and detector can be mounted to a motorized rotor which rotates around the gantry on a rail and bearing system. In another embodiment, the source and translatable detector remain fixed on a support, such as a table, while the object rotates on a turntable or rotatable stage.

The invention also relates to a method of imaging an object comprising projecting a beam of radiation in a first trajectory, the beam traveling through a first region of the object and onto a detector located at a first position; translating the detector to a second position in a direction that is substantially normal to the first trajectory; and altering the trajectory of the beam so that the beam travels through a second region of the object and onto the detector located at the second position. Preferably, the beam of radiation comprises a cone-beam or fan-beam of x-ray radiation, and the detected radiation is used to produce two-dimensional planar or three-dimensional computerized tomographic (CT) object images.

In one aspect, the invention is able to image objects larger than the field-of-view of the detector in a simple and straightforward manner by utilizing a detector positioner that translates the detector array to multiple positions, thus providing an effectively large field-of-view using only a single detector array having a relatively small size. In addition, a beam positioner permits the trajectory of the beam to follow the path of the translating detector, which advantageously enables safer and more efficient dose utilization, as only the region of the target object that is within the field-of-view of the detector at any given time needs to be exposed to harmful radiation.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-C are schematic diagrams showing an x-ray scanning system with a translating detector array according to one embodiment of the invention;

FIGS. 2A-D are side and perspective views illustrating the x-ray source and detector of the system of FIG. 1;

Figure 6A:
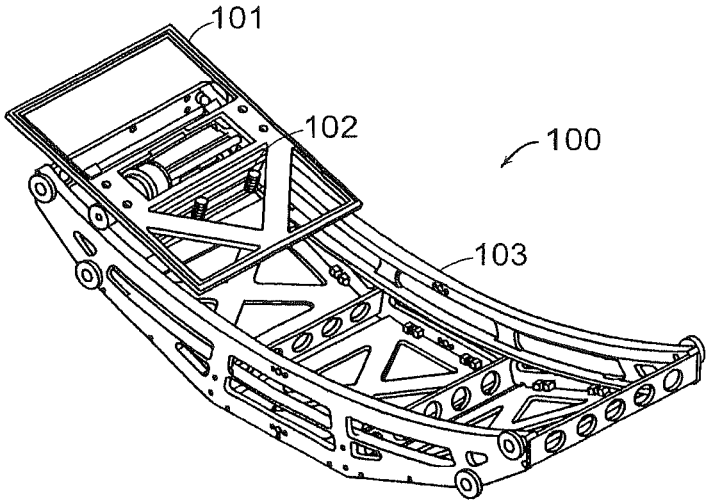
Figure 6B:
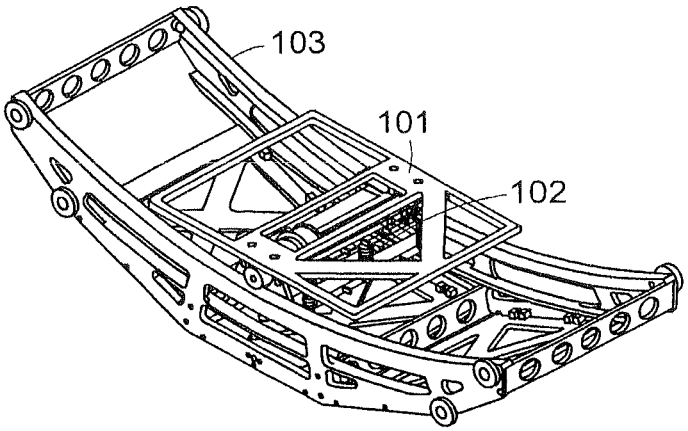
Figure 6C:
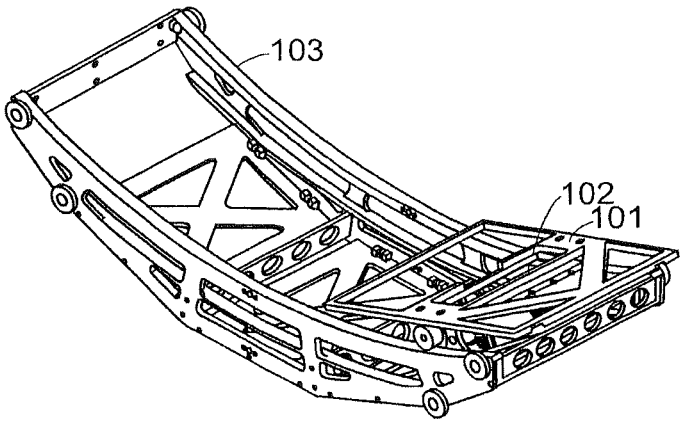
Figure 7:
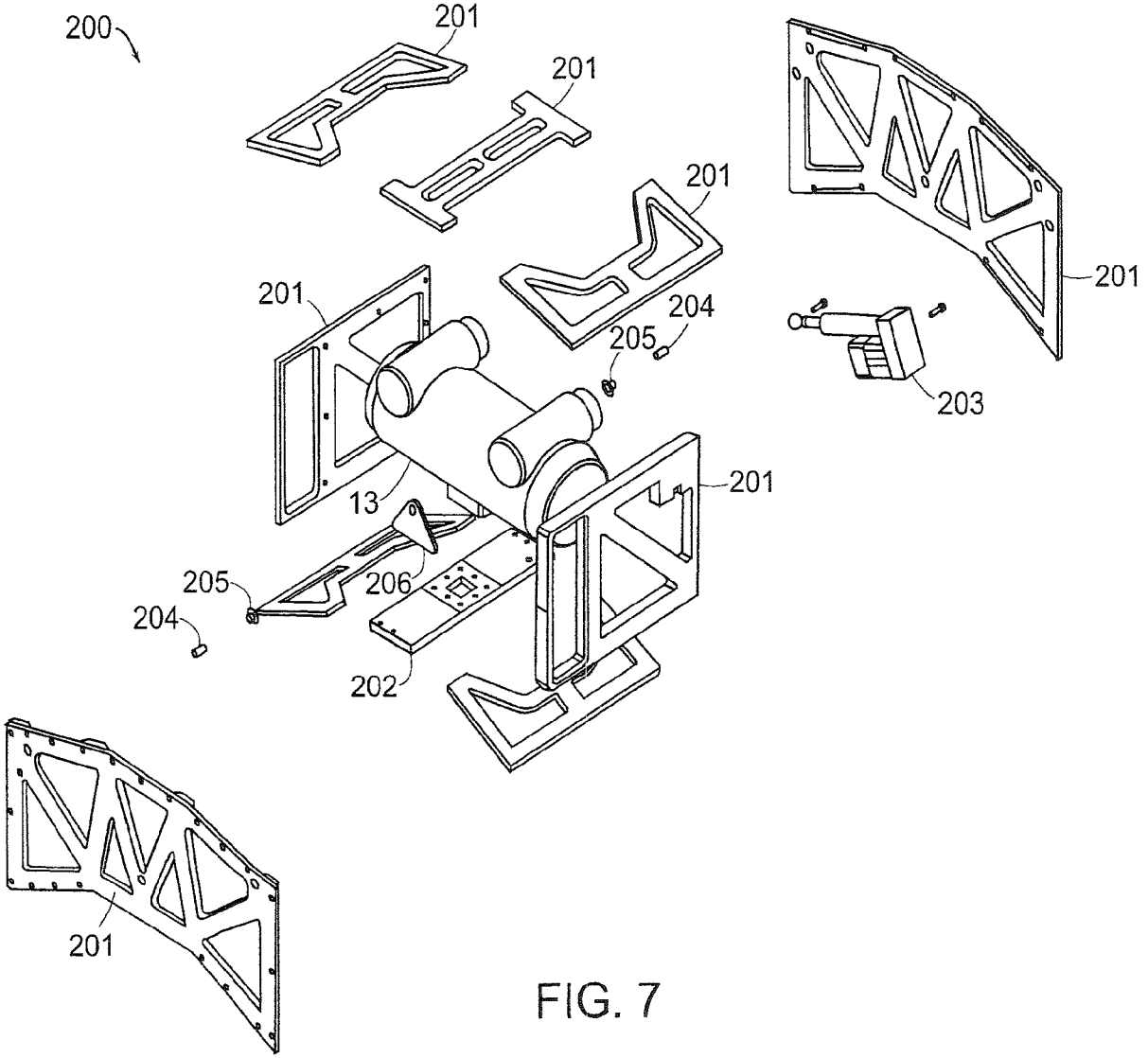
Figure 8:
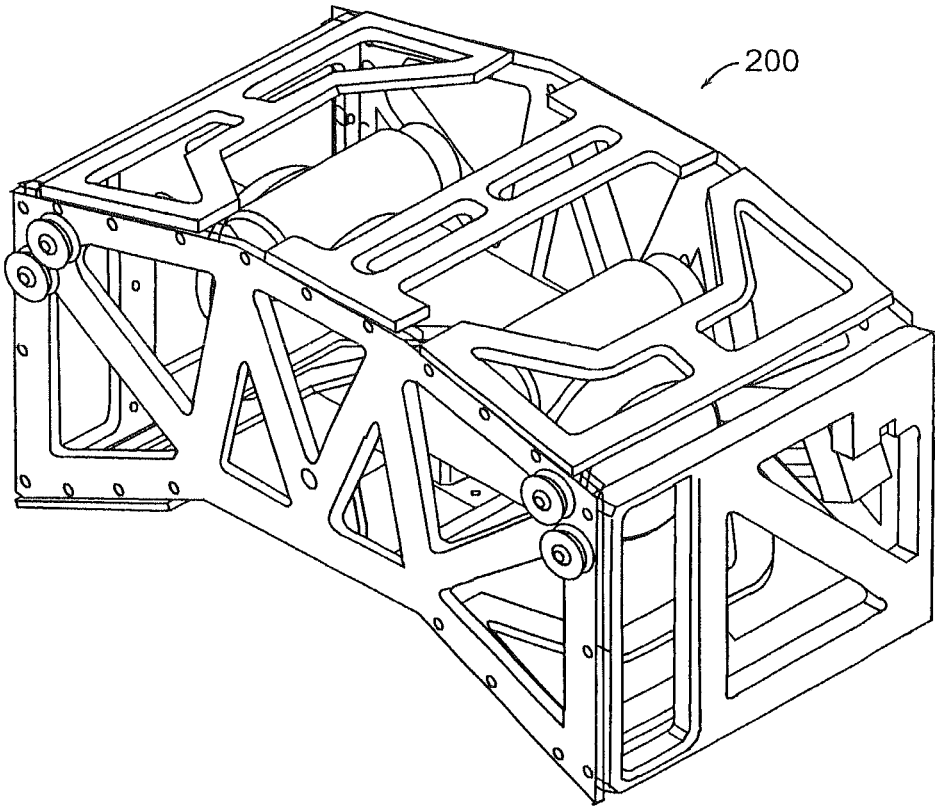
Figure 9A:
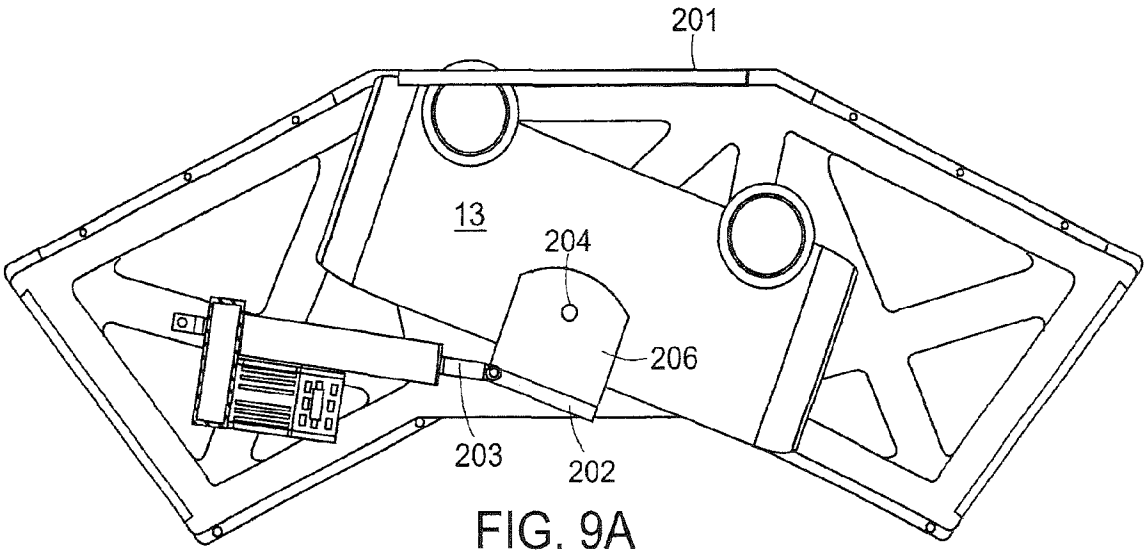
Figure 9B:
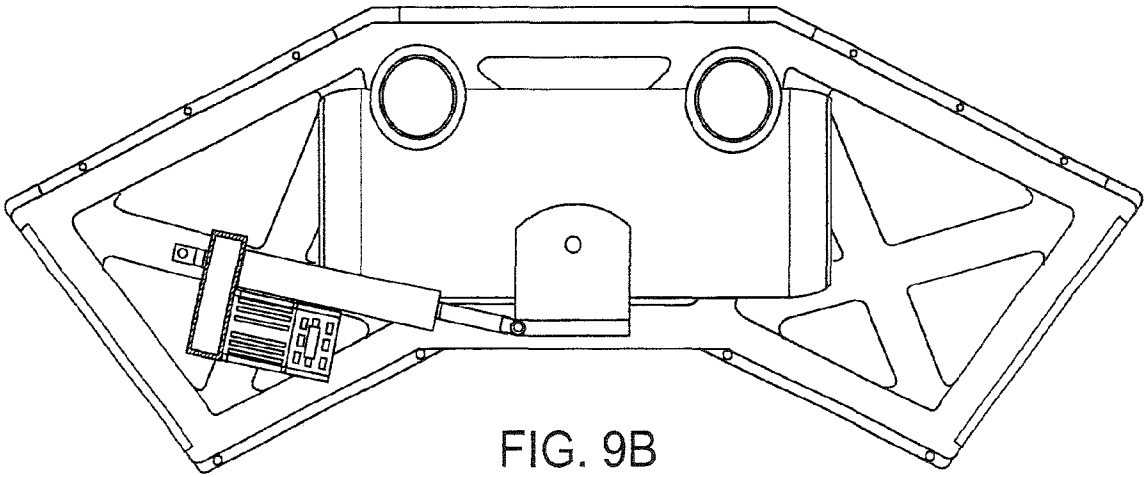
Figure 9C:
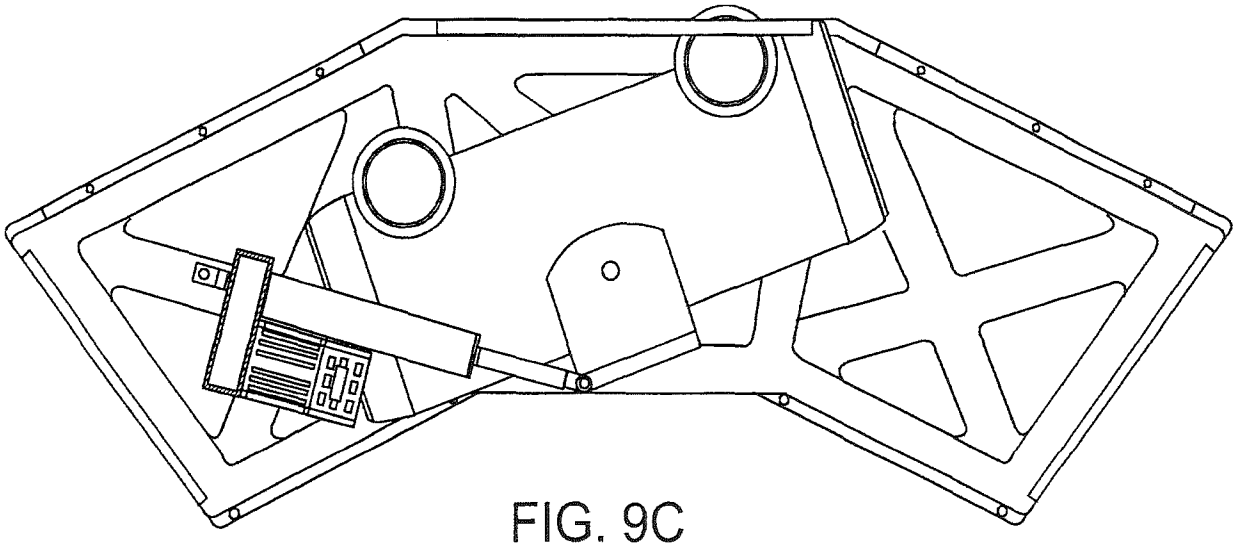
Figure 10:
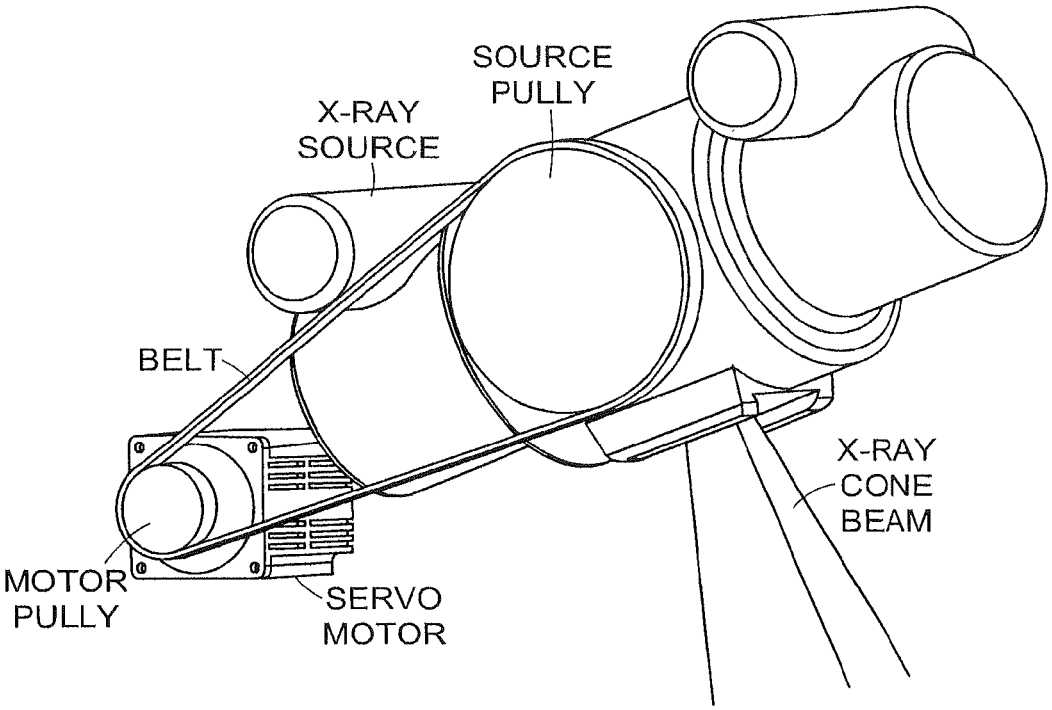
Figure 11:
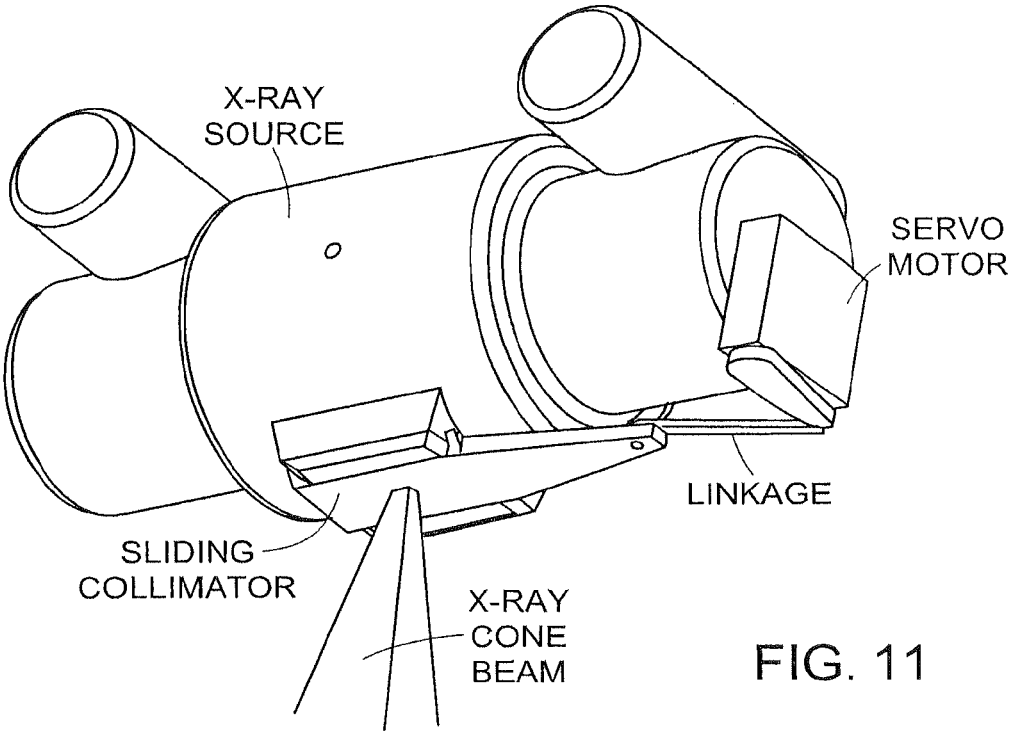
Figure 12:
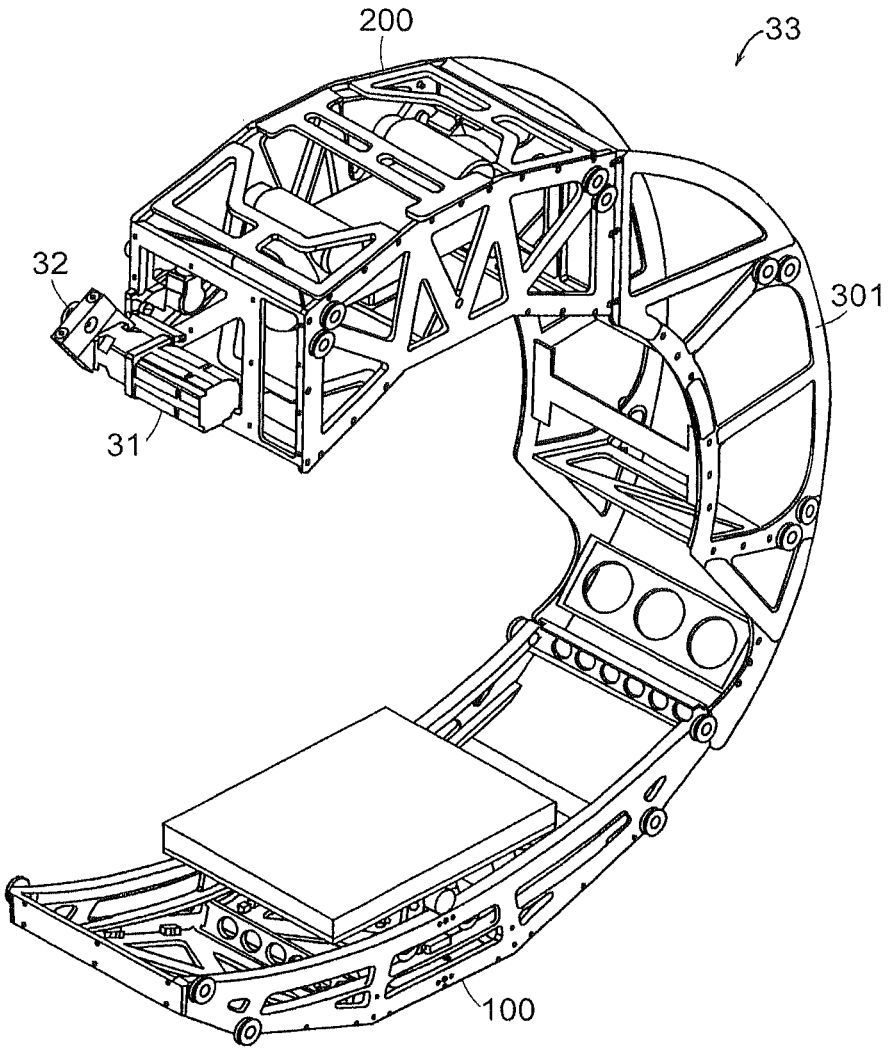
Figure 13:
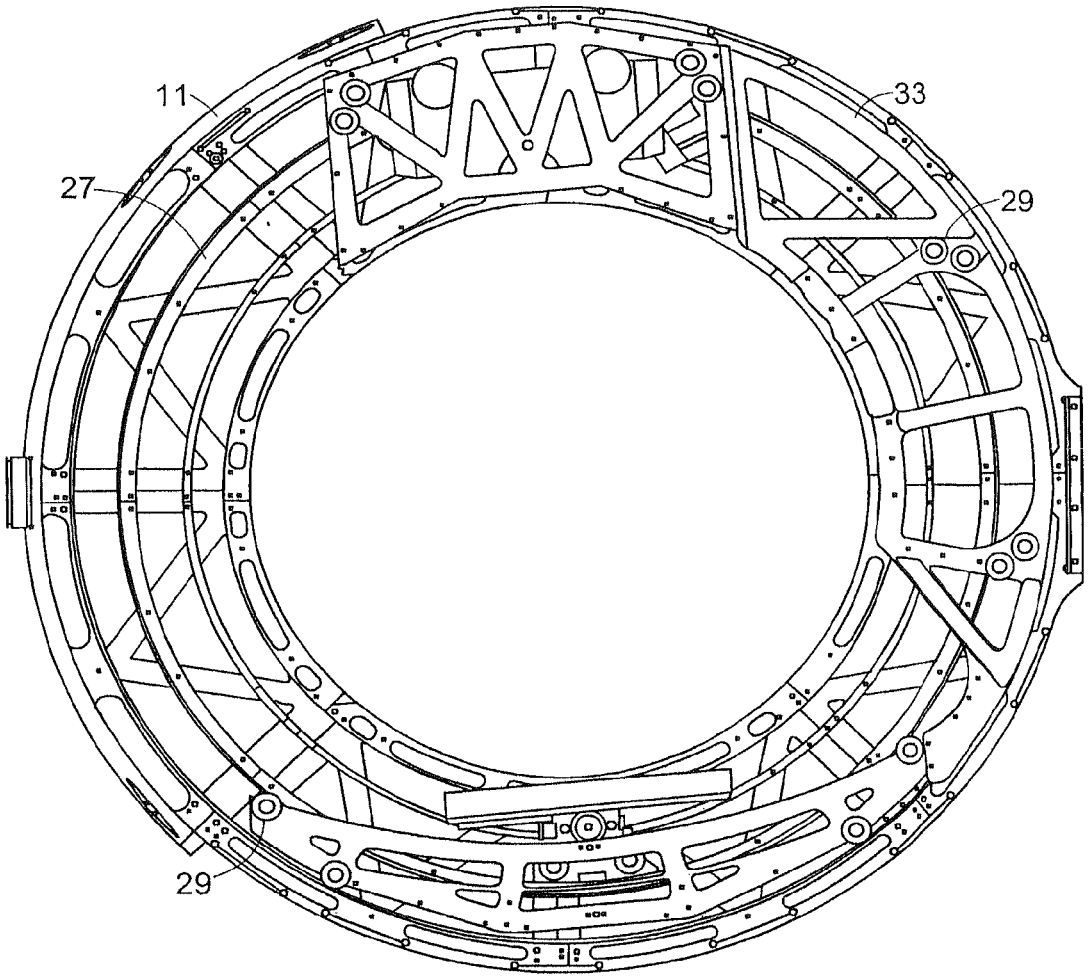
Figure 14:
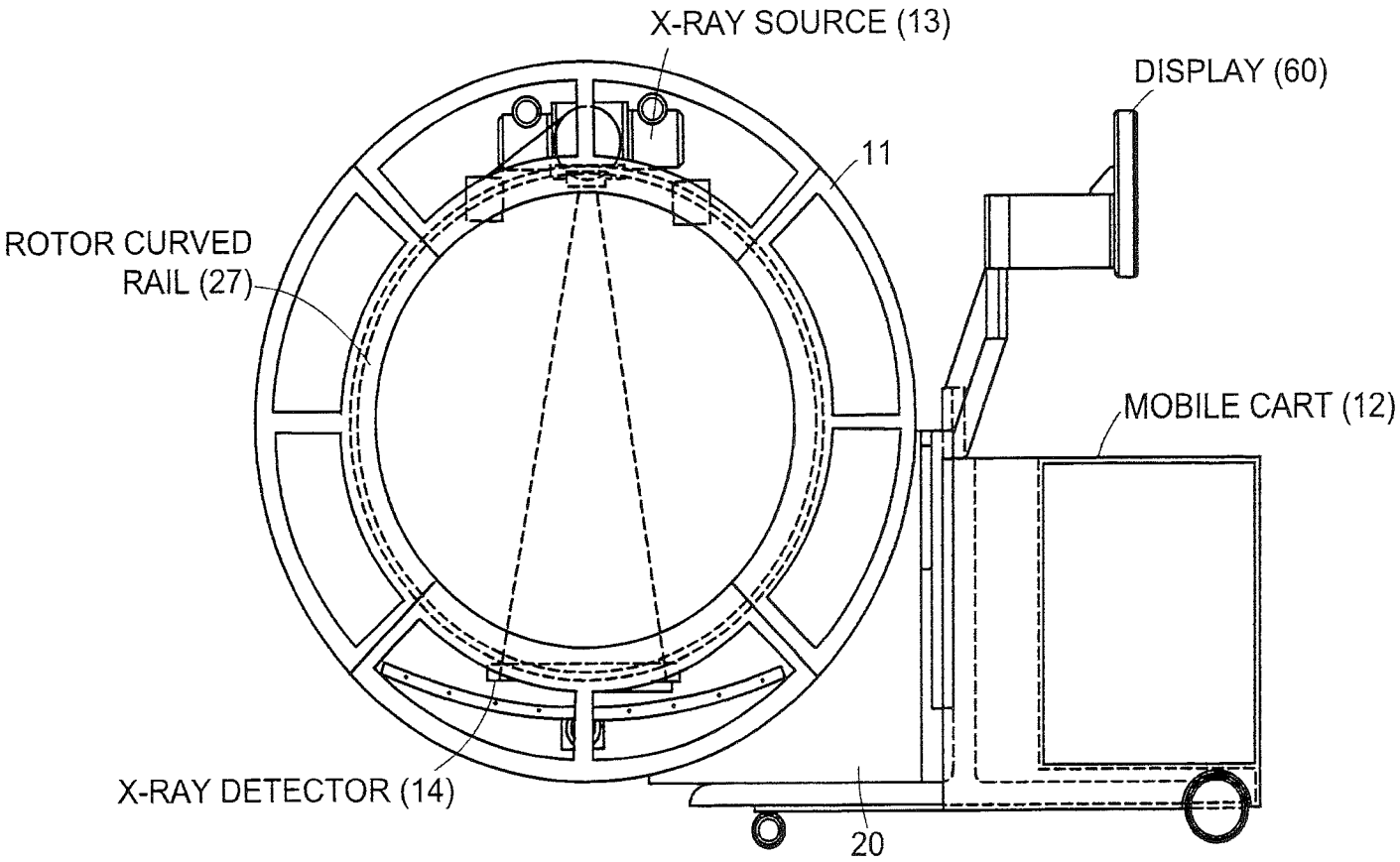
Figure 15:
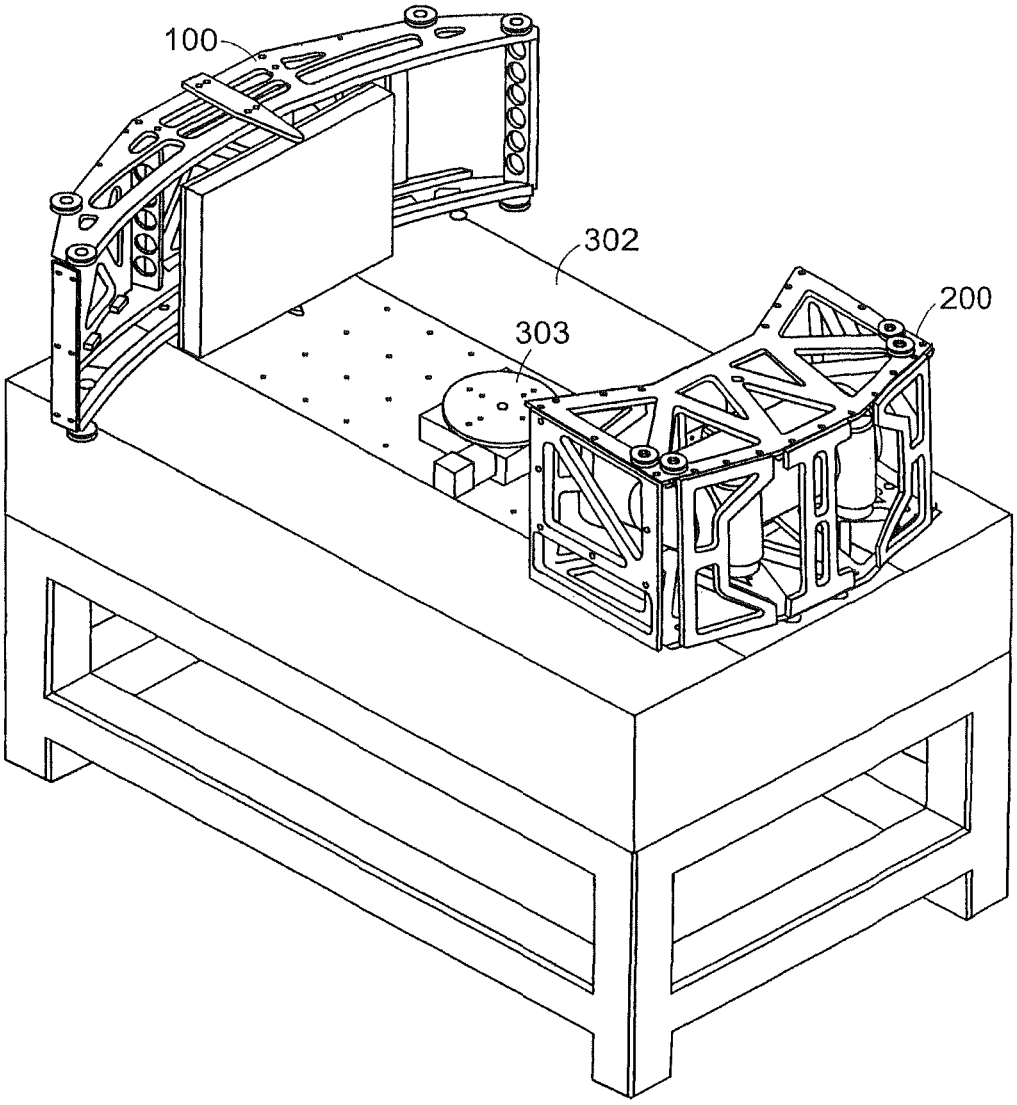

FIGS. 6A-C shows the x-ray detector positioning stage translating to three positions;

FIG. 7 is an exploded view of an x-ray source and source positioning stage according to one embodiment of the invention;

FIG. 8 is a perspective view of an assembled x-ray source and positioning stage;

FIGS. 9A-C shows an x-ray source tilted to three positions by a linear actuator, according to one embodiment of the invention;

FIG. 10 shows a motorized belt and pulley system for tilting an x-ray source to multiple positions, according to another embodiment;

FIG. 11 shows a motorized sliding collimator for directing an x-ray beam to multiple detector positions, according to yet another embodiment;

FIG. 12 is a perspective view of a rotor assembly for rotating an x-ray source and detector within a gantry;

FIG. 13 is a cutaway side view showing the rotor assembly within a gantry ring;

FIG. 14 is a schematic illustration of a mobile cart and gantry assembly for tomographic and planar imaging of large field-of-view objects according to one embodiment;

FIG. 15 illustrates a table-top x-ray assembly with rotatable stage for tomographic and planar imaging of large field-of-view objects according to yet another embodiment; [and]

Figure 16:
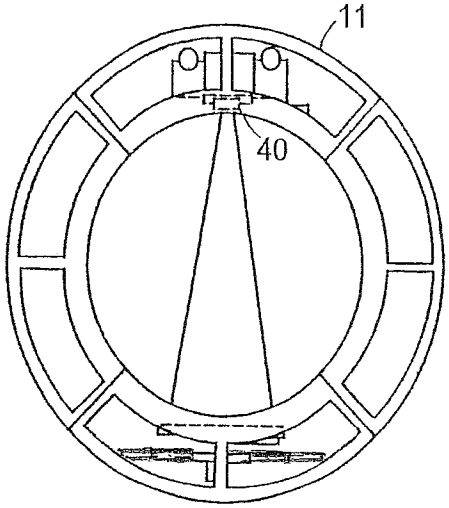

FIG. 16 shows a detector that is translated along a line[.];

*FIG. 17 is a schematic diagram showing an x-ray scanning system according to one embodiment of the invention;*

*FIGS. 18A-18D show the x-ray scanning system of FIG. 17 acquiring quasi-simultaneous anterior/posterior and lateral images of a spine throughout a rotation of a motorized rotor within the O-shaped x-ray gantry;*

*FIG. 19 shows an x-ray detector array capturing multiple x-ray images throughout a 360 degree rotation;*

*FIG. 20 illustrates a motorized rotor assembly for rotating an x-ray source and detector array within the gantry ring of an x-ray scanning device of the invention;*

*FIG. 21A is a cutaway side view of a gantry ring having a motorized rotor assembly mounted inside the ring;*

*FIG. 21B is a side view of a gantry ring enclosing a motorized rotor assembly;*

*FIGS. 22A-22E illustrate an x-ray imaging apparatus having a cable management system for rotating an x-ray source and detector array around the interior of the gantry ring;*

*FIG. 23 shows a gantry ring positioning unit in a parked mode;*

*FIG. 24 shows the gantry ring positioning unit in a fully extended lateral position;*

*FIG. 25 shows the gantry ring positioning unit in a fully extended vertical position;*

*FIG. 26 shows the gantry ring positioning unit in a fully extended tilt position;*

*FIG. 27 shows the gantry ring and positioning unit in fully extended lateral, vertical, and tilt positions;*

*FIG. 28 illustrates an x-ray imaging apparatus having a vertical-axis gantry for imaging a standing or sitting patient;*

*FIG. 29 is a schematic diagram showing an x-ray scanning system with a partially open gantry ring according to one embodiment of the invention;*

*FIGS. 30A and 30B show two side views of the x-ray scanning system of FIG. 29 with a hinged gantry segment in fully open and fully closed positions;*

*FIG. 31 shows an x-ray scanning system with a detachable gantry segment;*

*FIG. 32 shows an x-ray scanning system with a piggy back gantry segment;*

*FIG. 33 shows an x-ray scanning system with a telescoping gantry segment;*

*FIG. 34 shows an x-ray scanning system with a vertical lift gantry segment;*

*FIG. 35 shows an x-ray scanning system with a pivoted gantry segment;*

*FIG. 36 illustrates a gantry ring for an x-ray scanner system with a hinged gantry segment and a latching mechanism in an open and unlocked position;*

*FIG. 37 shows the gantry ring of FIG. 36 with the gantry segment and latching mechanism and a closed and unlocked position;*

*FIG. 38 shows the interior of a hinged gantry segment with rail and bearing assembly and latching mechanism;*

*FIG. 39 shows the interior of a hinged gantry segment with rail and bearing assembly and latching mechanism;*

*FIG. 40 illustrates a motorized rotor assembly for rotating an x-ray source and detector array within the gantry ring of an x-ray scanning device of the invention;*

*FIGS. 41A-41C are schematic illustrations of a patient entering an x-ray scanning device through an open hinged segment of the gantry ring and the patient inside the closed gantry ring;*

*FIG. 42 illustrates an x-ray imaging apparatus having a vertical-axis gantry with a detachable gantry segment for imaging a standing or sitting patient; and*

*FIGS. 43A-43E illustrate an x-ray imaging apparatus having a cable management system for rotating an x-ray source and detector array 360° around the gantry ring.*

Corresponding reference numerals indicate corresponding parts throughout the several views of the drawings.

DETAILED DESCRIPTION

Example embodiments will now be described more fully with reference to the accompanying drawings.

FIGS. 1A-C schematically illustrate an x-ray scanning system with a translating detector array according to one embodiment of the invention. The scanning system shown in FIGS. 1A-C includes gantry 11, which in this embodiment comprises a generally circular, or "O-shaped," housing having a central opening into which an object being imaged is placed. The gantry 11 contains an x-ray source 13 (such as a rotating anode pulsed x-ray source) that projects a beam of x-ray radiation 15 into the central opening of the gantry, through the object being imaged, and onto a detector array 14 (such as a flat panel digital detector array) located on the opposite side of the gantry. The x-rays received at the detector 14 can then be used to produce a 2D planar or 3D tomographic object reconstruction images using well-known techniques.

Figures 2A, 2B, 2C, 2D:
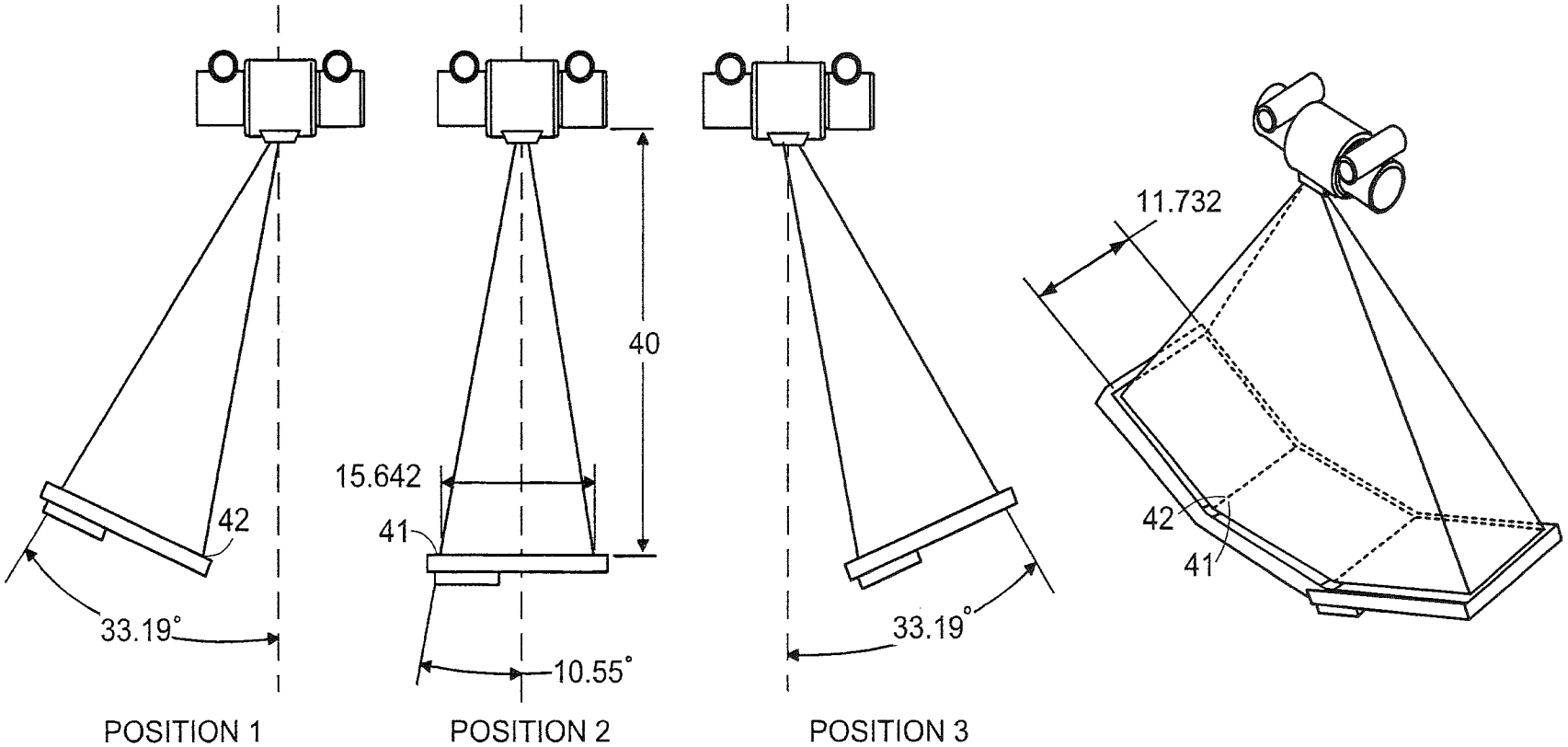

The detector 14 is translated to multiple positions along a line or arc in a direction that is generally normal to the trajectory of beam 15. This permits the detector to capture images of objects that are wider than the field-of-view of the detector array. FIGS. 1A-1C show the large field-of-view imaging area when the detector is translated to three positions along an arc opposite the x-ray source. This is more clearly illustrated in FIGS. 2A-C, which are side views of the source and detector as the detector translates to three different positions. FIG. 2D is a perspective view showing the resultant large imaging field-of-view by combining the data obtained at all three source and detector positions. As shown in FIGS. 2A-C, as the detector moves to each subsequent position, the last column of detector pixels 41 is positioned adjacent to the location of the leading column of pixels 42 from the prior detector position, thereby providing a large "effective" detector having a wide field-of-view, as shown in FIG. 2D. The image obtained is a combination of the three images abutted against one another, resulting in a large field-of-view using only a single detector array having a relatively small size. The detector 14 being translated along a line is illustrated in FIG. 16.

The source 13 preferably includes a beam positioning mechanism for changing the trajectory of the beam 15 from a stationary focal spot 40, so that the beam follows the detector as the detector translates, as shown in FIGS. 1A-C. This permits safer and more efficient dose utilization, as generally only the region of the target object that is within the field-of-view of the detector at any given time will be exposed to potentially harmful radiation.

Preferably, the translational movement of the detector and the trajectory of the x-ray beam can be automatically coordinated and controlled by a computerized motor control system.

Figure 3:
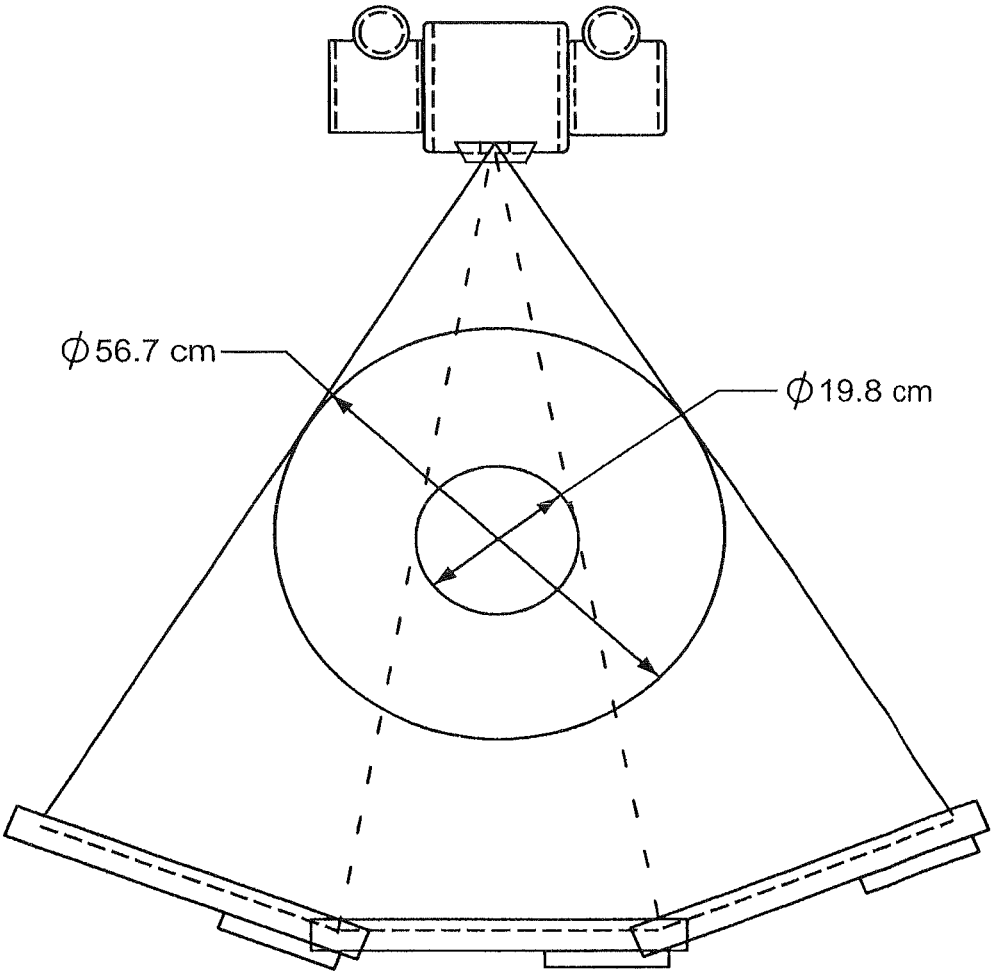
FIG. 3 illustrates the wide field-of-view achievable with the translating detector system of the present invention.

FIG. 3 illustrates the large field-of-view obtainable using the translating detector array of the present invention, as compared to the field-of-view of the same array in a conventional static configuration. The small and large circles represent varying diameters of the region centered on the axis of the imaging area that is within the field-of-view of the detector for the non-translatable and translatable arrays, respectively. The diameter of this imaging region is approximately half the width of the detector, since the beam diverges in the shape of a cone as it projects from the focal spot of the source onto the detector array. As shown in FIG. 3, the diameter of this imaging region can be greatly increased by translating the detector array and scanning the x-ray beam to multiple positions along a line or arc on the gantry.

In one aspect, the x-ray source 13 and translatable detector 14 are rotatable around the interior of the gantry, preferably on a motorized rotor, to obtain large field-of-view x-ray images from multiple projection angles over a partial or full 360-degree rotation. Collection of multiple projections throughout a full 360-degree rotation results in sufficient data for three-dimensional cone-beam tomographic reconstruction of the target object.

Figure 4:
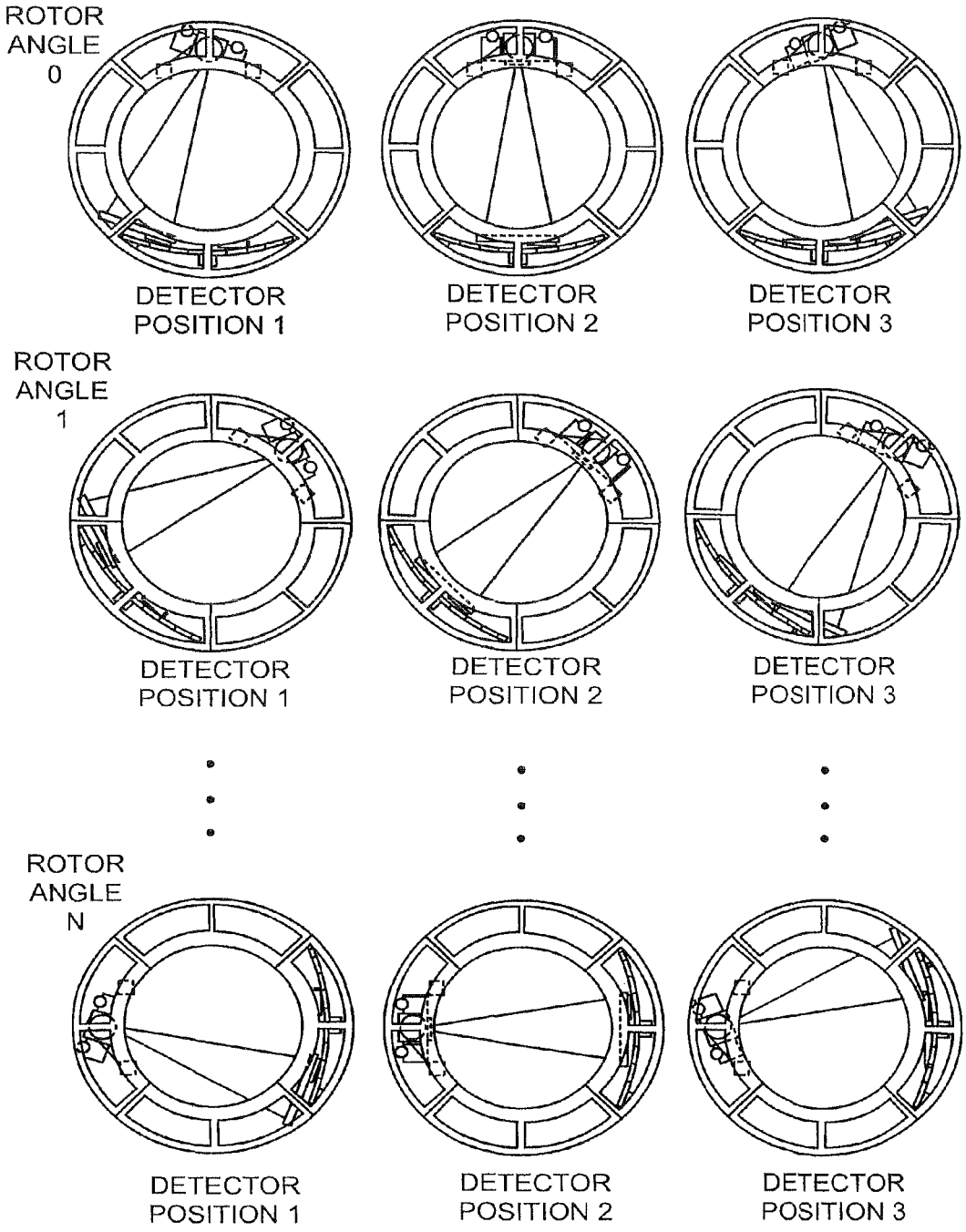
FIG. 4 is a schematic diagram showing a data collection matrix of an x-ray scanner system according to one embodiment of the invention.

As shown in the matrix diagram of FIG. 4, there are at least two methods for obtaining large field-of-view images over a partial or full 360-degree rotational scan of the target object. In the first method, for each rotational angle of the source and detector within the gantry, the detector is translated to two or more positions, capturing x-ray images at each detector position. This is shown in the top row of the matrix diagram of FIG. 4, where the x-ray source and detector stage are maintained at Rotor Angle 0, while the detector translates on the stage to Detector Positions 1-3. The rotor carrying the x-ray source and detector stage then rotate to a second position on the gantry, Rotor Angle 1, and the detector again translates to the three detector positions. This process repeats as the x-ray source and detector stage rotate through N rotor positions on the gantry to obtain large field-of-view object images over a full 360-degree scan.

In a second method, for each position of the translating detector, the source and detector stage perform a partial of full 360-degree rotation around the target object. This is shown in the leftmost column of the matrix diagram of FIG. 4, where detector is maintained at Detector Position 1, while the source and detector stage rotate within the gantry to Rotor Angles 0 through N. Then, as shown in the center column of FIG. 4, the detector is translated to Detector Position 2, and the source and detector stage are again rotated to Rotor Angles 0 through N. This process is repeated for each position of the translating detector array, with the source and detector stage performing a partial or full scan around the target object for each detector position.

Figure 5:
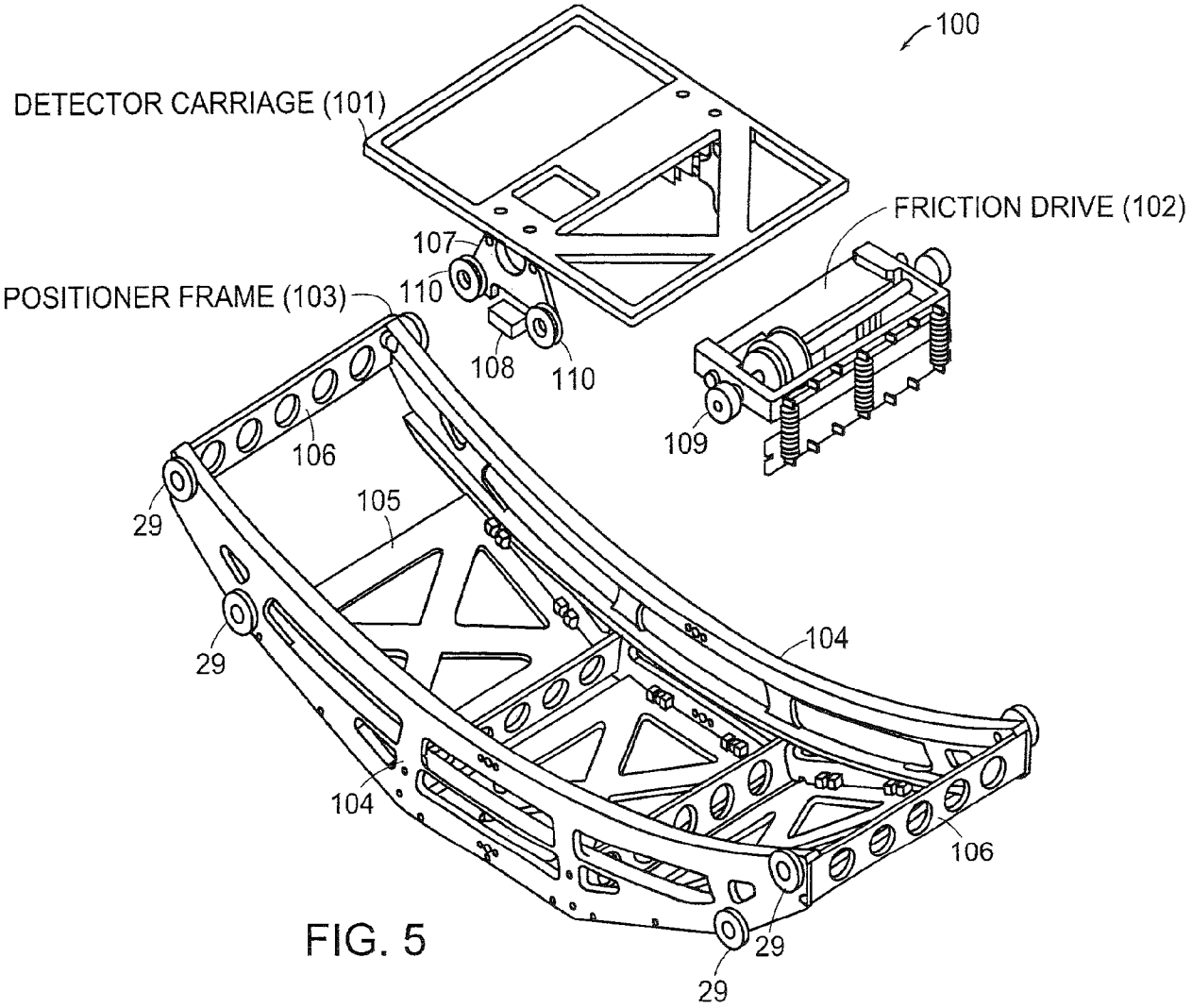
FIG. 5 is an exploded view of an x-ray detector positioning stage according to one embodiment.

Turning now to FIG. 5, an x-ray detector positioner 100 according to one embodiment of the invention is shown in exploded form. The positioning stage comprises a detector carriage 101 for holding the detector, a friction drive 102 which attaches to the detector carriage, and a positioner frame 103 upon which the detector carriage is movably mounted, The positioner frame includes two parallel side walls 104, a base 105, and a series of lateral frames 106 extending between the side walls. The interior of the side walls 104 include three main concentric surfaces extending the length of the frame. On top of each side wall 104 is a flat surface upon which a friction wheel 109 is driven, in the center is a v-groove rail on which a pair of v-groove rollers 110 ride, and on the bottom is another flat surface upon which a linear encoder tape is affixed.

In the embodiment shown, the concentric radii of the components of the curved side rails vary as a function of a circumscribed circle centered at the focal spot of an x-ray source. The central ray or line that connects the focal spot to the center pixel of the detector array is essentially perpendicular to the flat face of the detector array. By moving the translating detector components along the defined curved side rails, the face of the detector translates tangentially to the circle circumscribed by connecting the ray or line that connects the focal spot to the center pixel of the detector array. Other embodiments include a circle with infinite radius, in which case the curved side rails become straightened along a flat plane or line.

The friction drive 102 consists of a servomotor, gear head, belt drive, axle, and friction wheels 109. The friction drive is mounted to the detector carriage 101 by brackets 107. The friction wheels 109 are preferably spring-loaded and biased against the flat top surface of the side walls 104. The rollers 110 are mounted to brackets 107, and pressed into the central v-grooves of the positioner side walls 104. The v-groove rollers 110 precisely locate the detector carriage 101 as well as allow loading from any direction, thus enabling the accurate positioning of the translated detector array independent of gantry angle or position. The friction wheel 109 minimizes the backlash in the positioning system. In addition, a read head 108 is located on a detector carriage bracket 107 for reading the encoder tape affixed to the bottom flat surface of the positioner side wall 104. The read head 108 provides position feedback information to the servomotor for precise positioning of the detector carriage along the concentric axis of travel. The x-ray detector positioner 100 can also include bearings 29 attached to side walls 104 for rotating the entire detector assembly around the interior of a gantry, as described in further detail below.

Referring to FIGS. 6A-C, the assembled detector positioner 100 is shown translating the detector carriage 101 to multiple positions along an arc. In operation, the detector carriage 101 and friction drive assembly 102 are precisely moved by the servomotor along the concentric axis of the positioning frame and accurately positioned by the linear encoder system. Three positions are shown in FIGS. 6A-C, although the detector carriage 101 may be precisely positioned at any point along the arc defined by the positioner frame 103. The compact nature of the friction drive 102 allows for maximum translation of the detector carriage 101 while the drive 102 remains completely enclosed within the positioner frame 103, and allows the distal ends of the detector carriage to extend beyond the edge of the positioner frame (as shown in FIGS. 6A and 6C) to further increase the "effective" field-of-view obtainable with the detector.

As discussed above, the imaging system of the present invention preferably includes a radiation source with a beam positioning mechanism for changing the trajectory of the radiation emitted from a fixed focal spot, so that the beam may scan across multiple positions. One embodiment of an x-ray source stage 200 with a beam positioning mechanism is shown in FIG. 7. The stage comprises an outer wall frame 201 (shown in exploded form) which encloses the x-ray source 13, a swiveling x-ray source mount 202, and a servomotor linear actuator 203. The x-ray source is supported on the bottom by source mount 202 and from the sides by a pair of bushing mounts 206. The bushing mounts 206 are connected to the outer wall frame 201 by precision dowel pins 204 that are press-fit into bushings 205. The dowel pins 204 permit the bushing mounts 206, and thus the x-ray source 13 and source mount 202, to pivot with respect to the outer wall frame 201 pivoting motion. This pivoting motion is preferably centered at the focal spot of the x-ray source.

The precision servomotor linear actuator 203 is attached at one end to the outer wall frame 201, and at the other end to the swiveling x-ray source mount 202. By varying the length of the motorized linear actuator 203, the source mount 202 and x-ray source 13 can be pivoted about dowel pins 204 to tilt the x-ray source about its focal spot in a controlled manner. The fully assembled x-ray source stage is shown in FIG. 8.

The operation of the x-ray source and tilting beam positioning mechanism is shown in FIGS. 9A-9C. As the linear actuator moves from a fully retracted position (FIG. 9A) to a fully extended position (FIG. 9C) the x-ray source pivots about its focal spot, thus altering the trajectory of the emitted radiation beam. In this embodiment, the pivot point represents the center of a circle with a radius defined by the distance from the focal spot to the center pixel of the detector array. The pivot angle is computed by determining the angle defined by the line connecting the focal spot of the x-ray detector and the center pixel of the detector array. A computerized motion control system can be used to synchronize the x-ray source tilt angle with the position of a translating detector array so that the x-ray beam remains centered on the detector even as the detector translates to different positions.

Various other embodiments of an x-ray beam positioner can be employed according to the invention. For example, as shown in FIG. 10, the x-ray source can be tilted to multiple positions by a motorized belt and pulley system. In another embodiment shown in FIG. 11, the trajectory of the x-ray beam is altered by a sliding collimator that is driven by a servomotor.

As shown in FIG. 12, the x-ray source stage 200 and x-ray detector positioner 100 can be joined together by a curved bracket assembly 301 to produce a C-shaped motorized rotor assembly 33. The rigid bracket 301 maintains the source and detector opposed to one another, and the entire rotor assembly can be rotated inside an O-shaped x-ray gantry. The rotor assembly 33 can also include a motor 31 and drive wheel 32 attached at one end of the rotor for driving the rotor assembly around the interior of the gantry.

FIG. 13 is a cutaway side view of a gantry 11 which contains a C-shaped motorized rotor 33. The interior side walls of the gantry include curved rails 27 extending in a continuous loop around the interior of the gantry. The drive wheel 32 of the rotor assembly 33 contacts the curved rail 27 of the gantry, and uses the rail to drive the rotor assembly around the interior of the gantry. A rotary incremental encoder can be used to precisely measure the angular position of the rotor assembly within the gantry. The incremental encoder can be driven by a friction wheel that rolls on a concentric rail located within the sidewall of the gantry. The rotor assembly 33 also includes bearings 29, which mate with the curved rails 27 of the gantry to help guide the rotor assembly 33 as it rotates inside the gantry. The interior of the gantry ring 11 can include a slip ring that maintains electrical contact with the rotor assembly 33 to provide the power needed to operate the x-ray source, detector, detector positioner, and/or beam positioner, and also to rotate the entire assembly within the gantry frame. The slip ring can furthermore be used to transmit control signals to the rotor, and x-ray imaging data from the detector to a separate processing unit located outside the gantry. Any or all of the functions of the slip ring could be performed by other means, such as a flexible cable harness attached to the rotor, for example.

Although the rotor assembly of the preferred embodiment is a C-shaped rotor, it will be understood that other rotor configurations, such as O-shaped rotors, could also be employed. For example, a second curved bracket 301 could be attached to close the open end of the rotor, and provide a generally O-shaped rotor. In addition, the x-ray source and detector could rotate independently of one another using separate mechanized systems.

An x-ray scanning system 10 according to one aspect of the invention generally includes a gantry 11 secured to a support structure, which could be a mobile or stationary cart, a patient table, a wall, a floor, or a ceiling. As shown in FIG. 14, the gantry 11 is secured to a mobile cart 12 in a cantilevered fashion via a ring positioning unit 20. In certain embodiments, the ring positioning unit 20 enables the gantry 11 to translate and/or rotate with respect to the support structure, including, for example, translational movement along at least one of the x-, y-, and z-axes, and/or rotation around at least one of the x- and y-axes. X-ray scanning devices with a cantilevered, multiple-degree-of-freedom movable gantry are described in commonly owned U.S. Provisional Applications 60/388,063, filed Jun. 11, 2002, and 60/405,098, filed Aug. 21, 2002, the entire teachings of which are incorporated herein by reference.

The mobile cart 12 of FIG. 14 can optionally include a power supply, an x-ray power generator, and a computer system for controlling operation of the x-ray scanning device, including translational movement of the detector, and tilting movement of the x-ray source. The computer system can also perform various data processing functions, such as image processing, and storage of x-ray images. The mobile cart 12 preferably also includes a display system 60, such as a flat panel display, for displaying images obtained by the x-ray scanner. The display can also include a user interface function, such as a touch-screen controller, that enables a user to interact with and control the functions of the scanning system. In certain embodiments, a user-controlled pendant or foot pedal can control the functions of the scanning system. It will be understood that one or more fixed units can also perform any of the functions of the mobile cart 12.

The O-shaped gantry can include a segment that at least partially detaches from the gantry ring to provide an opening or "break" in the gantry ring through which the object to be imaged may enter and exit the central imaging area of the gantry ring in a radial direction. An advantage of this type of device is the ability to manipulate the x-ray gantry around the target object, such as a patient, and then close the gantry around the object, causing minimal disruption to the object, in order to perform x-ray imaging. Examples of "breakable" gantry devices for x-ray imaging are described in commonly-owned U.S. patent application Ser. No. 10/319,407, filed Dec. 12, 2002, now U.S. Pat. No. 6,940,941, issued Sep. 6, 2005, the entire teachings of which are incorporated herein by reference.

It will also be understood that although the embodiments shown here include x-ray imaging devices having O-shaped gantries, other gantry configurations could be employed, including broken ring shaped gantries having less than full 360 degree rotational capability.

Referring to FIG. 15, a table-top version of the large field-of-view scanning device is depicted. In this embodiment, the connector bracket, gantry, and rotor friction drive have been replaced by a rigid table mount 302 and a turntable 303 located in the center of the field of view. The turntable rotates the object to be imaged in a complete 360-degree rotation to capture projection images from any direction. The detector and source positioning assemblies 100, 200 are rigidly mounted a fixed distance from one another. The turntable 303 can be rigidly mounted to the table at any point along the ray connecting the x-ray focal spot and the center of the detector positioning assembly. The data collection techniques for this embodiment are essentially the same as those described for the x-ray gantry, except that in this case, it is the rotation of the object relative to the source and detector, rather than the rotation of the source and detector relative to the object, which effects the x-ray scanning.

The x-ray imaging systems and methods described herein may be advantageously used for two-dimensional and/or three-dimensional x-ray scanning. Individual two-dimensional projections from set angles along the gantry rotation can be viewed, or multiple projections collected throughout a partial or full rotation may be reconstructed using cone or fan beam tomographic reconstruction techniques. This invention could be used for acquiring multi-planar x-ray images in a quasi-simultaneous manner, such as described in commonly-owned U.S. patent application No. 10/389,268 entitled "Systems and Methods for Quasi-Simultaneous Multi-Planar X-Ray Imaging,", filed on Mar. 13, 2003, now U.S. Pat. No. 7,188,998, issued on Mar. 13, 2007, the entire teachings of which are incorporated herein by reference. Also, the images acquired at each detector position could be reprojected onto virtual equilinear or equiangular detector arrays prior to performing standard filtered backprojection tomographic reconstruction techniques, as described in commonly-owned U.S. Provisional Application No. 60/405,096, filed on Aug. 21, 2002.

*As discussed above, an x-ray scanning system is disclosed. The scanning system may include various embodiments which may include portions as discussed above and herein either separately or in combination. For example, FIG. 17 is a schematic diagram showing an x-ray scanning system 10 in accordance with one embodiment of the invention. The x-ray scanning system 10 includes a gantry 11' secured to a support structure, which could be a mobile or stationary cart, a patient table, a wall, a floor, or a ceiling. As shown in FIG. 17, the gantry 11' is secured to a mobile cart 12' in a cantilevered fashion via a ring positioning unit 20'. In certain embodiments, the ring positioning unit 20' translates and/or tilts the gantry 11' with respect to the support structure to position the gantry 11' in any number of imaging positions and orientations.*

*The mobile cart 12' of FIG. 17 can optionally include a power supply, an x-ray power generator, and a computer system for controlling operation of the x-ray scanning device and for performing image processing, storage of x-ray images, or other data processing functions. In a preferred embodiment, the computer system controls the positioning unit 20' to enable the gantry 11' to be quickly moved to a particular user-defined position and orientation. The computer preferably has a memory that is capable of storing positioning information relating to particular gantry positions and/or orientations. This stored positioning information can be used to automatically move the gantry to a pre-defined configuration upon demand.*

*The mobile cart 12' preferably also includes a display system 60', such as a flat panel display, for displaying images obtained by the x-ray scanner. The display can also include a user interface function, such as a touch-screen controller, that enables a user to interact with and control the functions of the scanning system. In certain embodiments, a user-controlled pendant or foot pedal can control the functions of the scanning system.*

*It will be understood that one or more fixed units can also perform any of the functions of the mobile cart 12'.*

*According to one aspect, the x-ray scanning system of the invention can be used to obtain two-dimensional x-ray images of an object, such as a patient, in multiple projection planes. In the embodiment shown in FIG. 17, the gantry 11' is a generally circular, or "O-shaped," housing having a central opening into which an object being imaged is placed. The gantry 11' contains an x-ray source 13' (such as a rotating anode pulsed x-ray source) that projects a beam of x-ray radiation 15' into the central opening of the gantry, through the object being imaged, and onto a detector array 14' (such as a flat panel digital detector array) located on the opposite side of the gantry. The x-rays received at the detector 14' can then be used to produce a two-dimensional image of the object using well-known techniques.*

*The x-ray source 13' is able to rotate around the interior of the gantry 11' in a continuous or step-wise manner so that the x-ray beam can be projected through the object, and through a common isocenter, at various angles over a partial or full 360 degree rotation. The detector array is also rotated around the interior of the gantry, in coordination with the rotation of the x-ray source, so that for each projection angle of the x-ray source, the detector array is positioned opposite the x-ray source on the gantry. The apparatus is thus able to obtain two-dimensional x-ray images of the targeted object in any projection plane over a partial or full 360 degree rotation.*

*The x-ray system of the invention can be operated in a static or in a multi-planar mode. In a static mode, a user selects a desired imaging plane in the target object, and the x-ray source and detector are rotated to the appropriate angle within the gantry. As shown in FIG. 18A, for example, the x-ray source and detector are at the top and bottom of the gantry, respectively, for acquisition of an anterior-posterior (AP) type patient image. Alternatively, or in addition, the gantry itself can be moved by positioning or tilting the gantry relative to the target object using the gantry positioning unit 20', as shown in FIG. 27. In static mode, the x-ray scanner can acquire and display a single x-ray image of the object, or can obtain multiple images of the object, and continuously update the display with the most recent image. In a preferred embodiment, the x-ray scanner obtains multiple object images in quick succession, and displays these images in real time (e.g. 30 frames per second) in a "cinematic" mode.*

*To change the imaging plane of the object, the x-ray source and detector can be rotated to another angle within the gantry. As shown in FIG. 18B, for example, the source and detector rotate 90 degrees in a clockwise direction for obtaining object images in a lateral plane. Alternatively or in addition, translating or tilting the entire gantry to a second position can change the imaging plane.*

*In multi-planar mode, the x-ray scanner obtains a series of images from multiple projection planes in rapid succession. The imaging system advantageously permits quasi-simultaneous multi-planar imaging using a single radiation*

*source. As shown in FIG. 18A, for example, the x-ray source 13' and detector 14' are initially positioned at the top and bottom of the gantry respectively and acquire a first x-ray image of the target object, which in this case is an anterior-posterior (AP) view of a patients spine. The source and detector then rotate 90 degrees clockwise within the fixed gantry to obtain a second x-ray image shown in FIG. 18B, which is a lateral view of the spine. These bi-planar AP/lateral images are obtained quasi-simultaneously, as there is no appreciable delay between the acquisition of the two images, other than the time it takes for the source to rotate between projection angles on the gantry. Additional AP/lateral images can be obtained and continuously updated by alternatively rotating the source and detector between two projection angles, such as the two perpendicular projections shown FIGS. 18A and 18B. In a preferred embodiment, however, quasi-simultaneous multi-planar images are obtained and updated in real time by continuously rotating the source and detector over a full 360 degree rotation, obtaining images at desired rotational increments. As shown in FIGS. 18A and 18B, for example, four bi-planar images, including two AP images, and two lateral images, can be obtained in quick succession during a single 360 degree rotation of the source and detector. These images can be displayed individually, sequentially, side-by-side, or in any desired manner.*

*A further illustration of the quasi-simultaneous multi-planar imaging of the invention is shown in FIG. 19. Here, a rotatable detector array is shown capturing quasi-simultaneous x-ray images of ten incremental projection planes over a full 360 degree rotation. These images are captured continuously, or in a step wise fashion. They can be displayed individually, side-by-side, sequentially in a cinematic mode, or in any desired manner.*

*As shown in FIG. 17, the x-ray source 13' and detector array 14' can be secured to a C-shaped motorized rotor assembly 33'. The rigid rotor assembly maintains the source and detector opposed to one another while the entire rotor assembly rotates inside the gantry. As shown in FIGS. 20 and 21A, the rotor assembly 33' also includes a motor 31' and drive wheel 32' for driving the rotor assembly around the interior of the gantry. As shown in FIG. 21A, the interior side walls of the gantry include curved rails 27' extending in a continuous loop around the interior of the gantry. The drive wheel 32' of the rotor assembly 33' contacts the curved rail 27' of the gantry, and uses the tall to drive the rotor assembly around the interior of the gantry. A rotary incremental encoder can be used to precisely measure the angular position of the rotor assembly within the gantry. The incremental encoder can be driven by a friction wheel that tolls on a concentric rail located within the sidewall of the gantry. The rotor assembly 33' also includes bearings 29', which mate with the curved rails 27' of the gantry to help guide the rotor assembly 33' as it rotates inside the gantry. The interior of the gantry ring 11' can include a slip ring 102' that maintains electrical contact with the rotor assembly 33' to provide the power (e.g., from external power source 101') needed to operate the x-ray source/detector and to rotate the entire assembly within the gantry frame. The slip ring can also be used to transmit control signals to the rotor, and x-ray imaging data from the detector to a separate processing unit located outside the gantry, such as the mobile can 12' of FIG. 17. Any or all of the functions of the slip ring could be performed by other means, such as the cable management system described below.*

*Although the rotor assembly of the preferred embodiment is a C-shaped rotor, it will be understood that other rotor configurations, such as O-shaped rotors, could also be employed. In addition, the x-ray source and detector could rotate independently of one another using separate mechanized systems. Moreover, the x-ray source alone can rotate, with multiple detector arrays located at fixed positions around the interior of the gantry.*

*The detector array 14' shown in FIG. 20 comprises a two-dimensional flat panel solid-state detector array. It will be understood, however, that various detectors and detector arrays can be used in this invention, including any detector configurations used in typical diagnostic fan-beam or cone-beam imaging systems, such as C-arm fluoroscopes. A preferred detector is a two-dimensional thin-film transistor x-ray detector using scintillator amorphous-silicon technology.*

*For large field-of-view imaging, the detector 14' can be translated to, and acquire imaging data at, two or more positions along a line or arc opposite the x-ray source 13', such as via a motorized detector rail and bearing system. Examples of such detector systems are described in commonly owned U.S. Provisional Application No. 60/366,062, filed Mar. 19, 2002, the entire teachings of which are incorporated herein by reference.*

*FIGS. 22A-22E illustrate another embodiment of an x-ray imaging apparatus having a cable management system for rotating an x-ray source and detector array 360° around the interior of the gantry ring. In this embodiment, the power for the x-ray source/detector system, as well as for rotating the x-ray source/detector within the gantry, is provided (at least in part) by a cable harness 36' containing one or more cables. The cable harness 36' can also be used to transmit signals and data between the x-ray source/detector and an external processing unit.*

*The cable harness 36' is preferably housed in a flexible, linked cable carrier 37'. One end of the carrier 37' is fixed to a stationary object, such as the gantry 11' or the cart. The other end of the carrier 37' is attached to the motorized rotor assembly 33' which contains the x-ray source 13' and detector 14'. In the example shown in FIGS. 22A-22E, the rotor 33' starts at an initial position with the x-ray source 13' at the bottom of the gantry and the detector 14' at the top of the gantry (i.e. rotor angle=0°) as shown in FIG. 22A. The rotor 33' then rotates in a clockwise direction around the interior of the gantry, as illustrated in FIG. 22B (90°° rotation), FIG. 22C (180°° rotation), FIG. 22D (270°° rotation), and FIG. 22E (360°° rotation). In FIG. 22D, the rotor 33' has made a full 360°° rotation around the interior of the gantry 11', and the rotor is again at the initial position with the x-ray source 13' at the bottom of the gantry, and the detector 14' at the top of the gantry. During the rotation, the cable carrier 37' remains connected to both the rotor 33' and gantry 11', and has sufficient length and flexibility to permit the rotor 33' to easily rotate at least 360° from the start position. To perform another 360° rotation, the rotor 33' can rotate counterclockwise from the end position of the prior rotation (e.g. rotor angle=360° in FIG. 22E) until the rotor 33' returns to the initial position of FIG. 22A. For continuous rotation, this process can repeat itself indefinitely with the rotor making full 360° rotations in alternatively clockwise and counterclockwise directions.*

*As shown in FIGS. 23-27, the ring positioning unit 20' preferably enables the gantry 11' to translate and/or tilt with respect to the support structure. FIG. 23 shows a gantry ring positioning unit in a parked mode. FIG. 24 shows the translational motion of the positioning unit in a lateral direction relative to the cart. FIG. 25 shows translational movement of the positioning unit in a vertical direction*

*relative to the cart. FIG. 26 shows the tilting motion of the positioning unit relative to the cart. In FIG. 27, the entire gantry assembly is illustrated in fully extended lateral, vertical, and tilt positions. The ability of the gantry to translate and tilt in multiple directions allows for the acquisition of x-ray images in any desired projection plane, without having to continuously reposition the patient or the system. As discussed above, a control system can automatically move the gantry to a desired position or orientation, including to user-defined positions and orientations stored in computer memory, for x-ray imaging procedures. X-ray scanning devices with cantilevered, multiple-degree-of-freedom movable gantries are described in commonly owned U.S. Provisional Application No. 60/388,063, filed Jun. 11, 2002, and U.S. Provisional Application No. 60/405,098, filed Aug. 21, 2002, the entire teachings of which are incorporated herein by reference.*

*In the embodiments shown and described thus far, the central axis of the gantry is oriented essentially horizontally, so that an object being imaged, such as a patient, lies lengthwise in the imaging area. In other embodiments, however, the gantry may be aligned so that its central axis extends at virtually any angle relative to the patient or object being imaged. For instance, the central axis of the gantry can be aligned essentially vertically, as shown in FIG. 28. Here, the central opening of the gantry is concentric with the "cylinder" formed by the torso of a standing or sitting human. The entire imaging procedure can thus be performed while the patient remains in a standing or sitting position. Also, in addition to the medical procedures described, the vertical axis gantry may be useful for imaging other objects in which it is convenient to image the object while it is aligned in a standing or vertical orientation.*

*An imaging device of the present invention could also comprise a substantially O-shaped gantry that includes a segment that at least partially detaches from the gantry ring to provide an opening or "break" in the gantry ring through which the object to be imaged may enter and exit the central imaging area of the gantry ring in a radial direction. An advantage of this type of device is the ability to manipulate the x-ray gantry around the target object, such as a patient, and then close the gantry around the object, causing minimal disruption to the object, in order to perform x-ray imaging. Examples of "breakable" gantry devices for x-ray imaging are described in commonly-owned U.S. patent application Ser. No. 10/319,407, filed Dec. 12, 2002, the entire teachings of which are incorporated herein by reference.*

*It will also be understood that although the embodiments shown here include x-ray imaging devices having O-shaped gantries, other gantry configurations could be employed, including broken ring shaped gantries having less than full 360 degree rotational capability.*

*While this invention has been particularly shown and described with references to preferred embodiments thereof, it will be understood by those skilled in the art that various changes in form and details may be made therein without departing from the scope of the invention encompassed by the appended claims.*

*For instance, although the particular embodiments shown and described herein relate in general to x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.*

*As discussed above, an x-ray scanning system is disclosed. The scanning system may include various embodiments which may include portions as discussed above and herein either separately or in combination. For example, FIG. 29 is a schematic diagram showing an x-ray scanning system 10, such as a computerized tomographic (CT) x-ray scanner, in accordance with one embodiment of the invention. The x-ray scanning system 10 generally includes a gantry 11" secured to a support structure, which could be a mobile or stationary cart, a patient table, a wall, a floor, or a ceiling. As shown in FIG. 29, the gantry 11" is secured to a mobile cart 12" in a cantilevered fashion via a ring positioning unit 20". In certain embodiments, the ring positioning unit 20" enables the gantry 11" to translate and/or rotate with respect to the support structure, including, for example, translational movement along at least one of the x-, y-, and z-axes, and/or rotation around at least one of the x- and y-axes. X-ray scanning devices with a cantilevered, multiple-degree-of-freedom movable gantry are described in commonly owned U.S. Provisional Applications 60/388,063, filed Jun. 11, 2002, and 60/405,098, filed Aug. 21, 2002, the entire teachings of which are incorporated herein by reference.*

*The mobile cart 12" of FIG. 29 can optionally include a power supply, an x-ray power generator, a computer system for controlling operation of the x-ray scanning device and for performing image processing, tomographic reconstruction, or other data processing functions, and a display system, which can include a user interface for controlling the device. It will be understood that one or more fixed units can also perform these functions.*

*The gantry 11" is a generally circular, or "O-shaped," housing having a central opening into which an object being imaged is placed. The gantry 11" contains an x-ray source 13" (such as a rotating anode pulsed x-ray source) that projects a beam of x-ray radiation 15" into the central opening of the gantry, through the object being imaged, and onto a detector array 14" located on the opposite side of the gantry. The x-ray source 13" is also able to rotate 360 degrees around the interior of the gantry 11" in a continuous or step-wise manner so that the x-ray beam can be projected through the object at various angles. At each projection angle, the x-ray radiation beam passes through and is attenuated by the object. The attenuated radiation is then detected by a detector array opposite the x-ray source. Preferably, the gantry includes a detector array that is rotated around the interior of the gantry in coordination with the rotation of the x-ray source so that, for each projection angle, the detector array is positioned opposite the x-ray source on the gantry. The detected x-ray radiation from each of the projection angles can then be processed, using well-known reconstruction techniques, to produce a two-dimensional or three-dimensional object reconstruction image.*

*In a conventional CT x-ray scanning system, the object being imaged (typically a patient) must enter the imaging area lengthwise from either the front or rear of the gantry (i.e. along the central axis of the gantry opening). This makes it difficult, if not impossible, to employ CT x-ray scanning during many medical procedures, such as surgery, despite the fact that this is where CT scanning applications may be most useful. Also, the conventional CT x-ray scanner is a relatively large, stationary device having a fixed bore, and is typically located in a dedicated x-ray room, such as*

*in the radiology department of a hospital. CT scanning devices are generally not used in a number of environments, such as emergency departments, operating rooms, intensive care units, procedure rooms, ambulatory surgery centers, physician offices, and on the military battlefield. To date, there is not a small-scale or mobile CT scanning device, capable of producing high-quality images at relatively low cost, which can be easily used in various settings and environments, including during medical procedures.*

*In one aspect, the present invention relates to an improvement on the conventional design of an x-ray imaging device which overcomes these and other deficiencies. In particular, as shown in FIG. 29, the O-shaped gantry 11" includes a segment 16" that at least partially detaches from the gantry ring to provide an opening or "break" in the gantry ring through which the object to be imaged may enter and exit the central imaging area of the gantry ring in a radial direction. In FIG. 29, for instance, a segment 16" of the gantry 11" is secured to the gantry via a hinge 17" which allows the segment to swing out like a door from a fully closed position (see FIG. 2B) to a fully open position (see FIG. 30A). The object being imaged (for instance, a patient) can then enter the gantry from the open side (as opposed to from the front or rear side of the gantry, as in conventional systems), and the hinged segment can then be reattached to fully enclose the object within the gantry ring. (Alternatively, or in addition, the gantry in the open position can be moved towards the object in a lateral direction to position the object within the imaging area, and then the open segment can close around the object.)*

*In addition to the hinged door embodiment of FIGS. 29, 30A, and 30B, various other embodiments of the of the gantry assembly are shown in FIGS. 31-35. In each of these systems, a segment of the gantry at least partially detaches from the gantry ring to provide an opening or "break" in the gantry ring through which the object to be imaged may enter and exit the central imaging area of the gantry ring in a radial direction, and wherein the segment can then be reconnected to the gantry to perform 2D x-ray or 3D tomographic x-ray imaging.*

*In FIG. 31, for example, a gantry segment 16" is fully detachable from the fixed portion of the gantry ring 11", and can then be reattached to perform an x-ray imaging process. Similarly, in FIG. 32, the gantry segment 16" fully detaches from the ring to form an opening. In this case, however, the detached segment "piggy backs" on the gantry. This embodiment may include a linkage apparatus which allows the door 16" to detach away from the ring 11" and, while maintaining attached to the ring via the linkage apparatus, swing upwards and circumferentially onto the top of the fixed portion of the gantry ring 11".*

*FIG. 33 illustrates yet another embodiment, where the gantry opens by telescoping the detachable segment 16" with the fixed gantry ring 11". In one embodiment, a the detachable segment 16" can be attached to the gantry ring 11" with alignment pins. A release mechanism releases the pins, and the sidewalls of the segment 16" translate outward relative to the gantry ring, thus allowing the segment 16" to telescope over the fixed upper portion of the gantry ring 11".*

*In FIG. 34, the gantry opens by lifting a top segment 16" of the gantry off the ring, preferably via a vertical lift mechanism 18" which can be located on the cart 12".*

*FIG. 35 shows yet another embodiment with a pivoted gantry segment 16". This is similar to the hinged design of FIG. 29, except here the detachable segment is hinged to the gantry at the side of the gantry opposite the opening, so that the entire top half of the gantry lifts up to access the interior imaging area.*

*In any of these embodiments, the detachable gantry segment preferably includes a mechanism for securing the segment in place in a closed gantry configuration, yet also permits the segment to be easily detached to open or "break" the gantry ring.*

*In FIGS. 36-38, for example, a latching assembly 18" is used to secure or lock the hinged gantry segment 16" in place when the gantry is closed (for instance, during an x-ray imaging process). In a locked state, the hinged segment 16" is not permitted to pivot out from the closed gantry ring, and the x-ray source 13" and detector 14" can rotate 360 degrees around the inside of the closed gantry ring. However, the latching assembly 18" can also be easily unlocked, which permits the hinged segment 16" to be swung open.*

*In FIG. 36, for instance, the latching mechanism 18", which includes handle 21", linking members 22", 23", and upper and lower latches 24", 25", is in an unlocked position, while the hinged gantry segment 16" is in a fully open position. In FIG. 37, the gantry segment 16" is now in a closed position, but the latching mechanism 18" is still unlocked. As shown in FIG. 38, the latching mechanism 18" is locked by pulling handle 21" down into a locked position. The latching mechanism 18" can be easily unlocked by pushing the handle up to an unlocked position, and the hinged gantry segment 16" can then swing open.*

*In FIG. 39, the latching mechanism 18" is shown by way of an "end on" view of the interior of the open gantry segment 16". As shown here, spring-loaded alignment pins 34" on the hinged gantry segment 16" are driven into bushings 35" (see FIG. 36) on the fixed gantry 11" via a wedge-shaped latches 24", 25", causing the gantry segment 16" to be secured to the fixed gantry portion 11". The wedge-shaped latches 24",25" are driven by a linkage members 22", 23" connected to the handle 21" operated by a user. Also shown in this figure is a slip ring 26", which maintains electrical contact with the motorized rotor assembly 33" (see FIG. 40), and a curved rail 27", which guides the rotor assembly 33" as it rotates around the interior of the gantry 11", as will be described in further detail below. When the gantry is in a closed and locked position, the slip ring 26" and curved rail 27" of the detachable segment 16" align with the slip ring and curved rail of the fixed gantry, so that the motorized rotor assembly 30" (see FIG. 40) which carries the x-ray source and detector array can properly rotate within the gantry. During operation, the slip ring 26" preferably maintains electrical contact with the rotor assembly 30", and provides the power needed to operate the x-ray source/detector system, and to rotate the entire assembly within the gantry frame. The slip ring 26" can also be used to transmit x-ray imaging data from the detector to a separate processing unit located outside the gantry, such as in the mobile cart 12" of FIG. 29.*

*FIGS. 43A-43E illustrate another embodiment of an x-ray imaging apparatus having a cable management system for rotating an x-ray source and detector array 360° around the interior of the gantry ring. In this example, the power for the x-ray source/detector system, as well as for rotating the x-ray source/detector within the gantry, is provided (at least in part) by a cable harness 36" containing one or more cables, in much the same manner as the slip ring described above. The cable harness 36" can also be used to transmit signals and data between the x-ray source/detector and an external processing unit.*

*The cable harness 36" is preferably housed in a flexible, linked cable carrier 37". One end of the carrier 37" is fixed to a stationary object, such as the gantry 11" or the cart. The other end of the carrier 37" is attached to the motorized rotor assembly 33" which contains the x-ray source 13" and detector 14". In the example shown in FIGS. 43A-43E, the rotor 33" starts at an initial position with the x-ray source 13" at the top of the gantry and the detector 14" at the bottom of the gantry (i.e. rotor angle=0°) as shown in FIG. 43A. The rotor 33" then rotates in a clockwise direction around the interior of the gantry, as illustrated in FIG. 43B (90° rotation), FIG. 43C (180° rotation), FIG. 43D (270° rotation), and FIG. 43E (360° rotation). In FIG. 43E, the rotor 33" has made a full 360° rotation around the interior of the gantry 11", and the rotor is again at the initial position with the x-ray source 13" at the top of the gantry, and the detector 14" at the bottom of the gantry. During the rotation, the cable carrier 37" remains connected to both the rotor 33" and gantry 11", and has sufficient length and flexibility to permit the rotor 33" to easily rotate at least 360° from the start position. To perform another 360° rotation, the rotor 33" can rotate counterclockwise from the end position of the prior rotation (e.g. rotor angle=360° in FIG. 43E) until the rotor 33" returns to the initial position of FIG. 43A. For continuous rotation, this process can repeat itself indefinitely with the rotor making full 360° rotations in alternatively clockwise and counterclockwise directions.*

*FIGS. 39 and 40 show one example of a rail and bearing mechanism for rotating the x-ray source 13" and detector 14" inside the gantry for performing two-dimensional and/or three-dimensional x-ray imaging procedures. As shown in FIG. 40", a motorized rotor assembly 33" includes the x-ray source 13" and the detector array 14" held within a rigid frame 30" designed to maintain a constant spacing between the source and detector as the rotor assembly rotates inside the x-ray gantry. (Note that the motorized rotor is generally c-shaped, with an open region at least as large as the detachable segment 16" of the gantry frame, so that the rotor assembly does not obstruct the opening of the gantry.) The rotor assembly 30" also includes a motor 31" and gear 32" for driving the rotor assembly around the interior of the gantry. As shown in FIG. 39, the interior side walls of the gantry include curved rails 27" which extend in a continuous loop around the interior of the gantry when the gantry is in a closed position. The gear 32" of the rotor assembly 30" contacts the curved rail 27" of the gantry, and uses the rail to drive the rotor assembly around the interior of the gantry. The rotor assembly 30" also includes curve rail carriages 29", which mate with the curved rails 27" of the gantry to help guide the rotor assembly 30" as it rotates inside the gantry.*

*The detector array 14" shown in FIG. 40 comprises three two-dimensional flat panel solid-state detectors arranged side-by-side, and angled to approximate the curvature of the gantry ring. It will be understood, however, that various detectors and detector arrays can be used in this invention, including any detector configurations used in typical diagnostic fan-beam or cone-beam CT scanners. A preferred detector is a two-dimensional thin-film transistor x-ray detector using scintillator amorphous-silicon technology.*

*For large field-of-view imaging, a detector 14" can be translated to, and acquire imaging data at, two or more positions along a line or arc opposite the x-ray source 13", such as via a motorized detector rail and bearing system. Examples of such detector systems are described in commonly owned U.S. Provisional Application 60/366,062, filed Mar. 19, 2002, the entire teachings of which are incorporated herein by reference.*

*FIGS. 41A, 41B, and 41C show an embodiment of the scanner assembly 10 which is used for a medical imaging procedure. FIG. 41A, shows a patient 40" lying on a table 41" next to a mobile x-ray imaging apparatus 10 with a hinged segment 16" of the gantry ring 11" is fully open. The entire apparatus can then be moved in a lateral direction towards the patient (alternatively, or in addition, the patient can be moved towards the imaging apparatus), so that a region of interest of the patient is aligned within the x-ray gantry 11", as shown in FIG. 41B. Finally, as shown in FIG. 41C, the hinged segment 16" of the gantry 11" is closed, fully enclosing the patient within the gantry ring, and an x-ray imaging procedure is performed.*

*In the embodiments shown and described thus far, the central axis of the gantry is oriented essentially horizontally, so that an object being imaged, such as a patient, lies lengthwise in the imaging area. In other embodiments, however, the gantry may be aligned so that its central axis extends at virtually any angle relative to the patient or object being imaged. For instance, the central axis of the gantry can be aligned essentially vertically, as shown in FIG. 42. Here, the central opening of the gantry is concentric with the "cylinder" formed by the torso of a standing or sitting human. As in the previous embodiments, the gantry includes a segment 16" that at least partially detaches from the gantry ring 11" to provide an opening or "break" in the gantry ring through which the object to be imaged may enter and exit the central imaging area of the gantry ring in a radial direction. The patient can enter the gantry via this opening in a standing or sitting position, and the segment can be easily re-attached for an imaging procedure. The entire imaging procedure can thus be performed while the patient remains in a standing or sitting position. Also, in addition to the medical procedures described, the vertical axis gantry may be useful for imaging other objects in which it is convenient to image the object while it is aligned in a standing or vertical orientation.*

*The x-ray imaging apparatus described herein may be advantageously used for two-dimensional and/or three-dimensional x-ray scanning. Individual two-dimensional projections from set angles along the gantry rotation can be viewed, or multiple projections collected throughout a partial or full rotation may be reconstructed using cone or fan beam tomographic reconstruction techniques.*

*While this invention has been particularly shown and described with references to preferred embodiments thereof, it will be understood by those skilled in the art that various changes in form and details may be made therein without departing from the scope of the invention encompassed by the appended claims.*

*For instance, although the particular embodiments shown and described herein relate in general to computed tomography (CT) x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.*

*Also, while the embodiments shown and described here relate in general to medical imaging, it will be understood that the invention may be used for numerous other applica-*

*tions, including industrial applications, such as testing and analysis of materials, inspection of containers, and imaging of large objects.*

The detector arrays described herein include two-dimensional flat panel solid-state detector arrays. It will be understood, however, that various detectors and detector arrays can be used in this invention, including any detector configurations used in typical diagnostic fan-beam or cone-beam imaging systems, such as C-arm fluoroscopes. A preferred detector is a two-dimensional thin-film transistor x-ray detector using scintillator amorphous-silicon technology.

While this invention has been particularly shown and described with references to preferred embodiments thereof, it will be understood by those skilled in the art that various changes in form and details may be made therein without departing from the scope of the invention encompassed by the appended claims. For instance, although the particular embodiments shown and described herein relate in general to computed tomography (CT) x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.

Also, while the embodiments shown and described here relate in general to medical imaging, it will be understood that the invention may be used for numerous other applications, including industrial applications, such as testing and analysis of materials, inspection of containers, and imaging of large objects.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of operating an image apparatus, comprising:

positioning a detector to image at least a portion of a volume configured to hold an object larger than a field-of-view of the detector;

utilizing a detector positioner to translate the detector to multiple positions relative to the volume;

positioning a beam such that a trajectory of the beam follows the path of the translating detector; and moving a rotor within a gantry such that the beam follows the path of the translating detector;

wherein the detector and a beam source that emits the beam are movably mounted to the rotor.

2. A method of operating an image apparatus, comprising:

positioning a detector to image at least a portion of a volume configured to hold an object larger than a field-of-view of the detector;

[utilizing a detector positioner to translate] *translating* the detector to multiple positions relative to the volume;

positioning a beam such that a trajectory of the beam follows the path of the translating detector; and driving a beam source with a motor to pivotally move the beam source mounted on a swiveling source mount;

wherein the beam source is mounted to a source frame having at least two separated walls and a series of lateral members extending between the at least two separated walls and the swiveling source mount to pivotally hold the source relative to the source frame.

3. A method of operating an image apparatus, comprising:

positioning a detector to image at least a portion of a volume configured to hold an object larger than a field-of-view of the detector;

[utilizing a detector positioner to translate] *translating* the detector to multiple positions relative to the volume;

positioning a beam such that a trajectory of the beam follows the path of the translating detector; and moving a detector carriage relative to a detector frame having at least two separated walls and a series of lateral members extending between the at least two separated walls;

wherein the detector is mounted to the detector carriage to hold the detector and move the detector.

4. The method of claim 1, further comprising moving separately all of the beam source, the detector, and the rotor while obtaining images of the object.

5. The method of claim 1, further comprising rotating the rotor within an interior cavity of the gantry over a [360°] *360 degree* circumference of the gantry.

6. The method of claim 1, further comprising moving a source housing within a source stage to move the source housing about a central point to direct the beam onto the detector.

7. The method of claim 1, wherein the beam is projected by the beam source, and the trajectory of the beam is altered by tilting the beam source.

8. The method of claim 1, wherein translating the detector further includes translating the detector along an arc.

9. The method of claim 1, wherein translating the detector further includes translating the detector along a line.

10. A method of operating an image apparatus, comprising:

positioning a detector to image at least a portion of a volume configured to hold an object larger than a field-of-view of the detector, including:

positioning the detector at a first position within a gantry to image a first portion of the object;

positioning a beam such that the beam is detected by the detector at the first position;

moving the detector to a second position within the gantry to image the first portion of the object;

moving the beam [such that the beam is] *with the detector to be* detected by the detector at the second position; and moving a rotor within the gantry from a first angle to a second angle;

wherein both of the detector and a beam source that emits the beam are moveably mounted to the rotor.

11. The method of claim 10, further comprising:

moving all of the beam source, the detector, and the rotor to minimize exposure of the object to radiation while obtaining images of the object.

12. The method of claim 10, further comprising:

moving separately all of the beam source, the detector, and the rotor while obtaining images of the object.

13. The method of claim 10, wherein moving the detector to the second position within the gantry includes moving the detector along an arc.

14. The method of claim 10, wherein moving the detector to the second position within the gantry includes moving the detector along a line.

15. A method of operating an imaging apparatus, comprising:

positioning an object within an O-shaped gantry;

rotating a rotor carrying a source and a detector within an interior cavity of the gantry about the object;

positioning the detector to image a portion of the object that is larger than a field-of-view of the detector;

translating the detector to multiple positions relative to the object; and positioning a beam from the source such that a trajectory of the beam follows the path of the translating detector.

16. The method of claim 15, further comprising utilizing a detector positioner to translate the detector to the multiple positions.

17. The method of claim 15, wherein the detector is translated along one of an arc or along a line.

18. The method of claim 15, further comprising tilting the source at a focal point to change the trajectory of the beam to follow the path of the translating detector.

* * * * *